(12) United States Patent
Yekhanin et al.

(10) Patent No.: US 11,710,538 B2
(45) Date of Patent: Jul. 25, 2023

(54) EFFICIENT POLYMER SYNTHESIS

(71) Applicant: MICROSOFT TECHNOLOGY LICENSING, LLC, Redmond, WA (US)

(72) Inventors: Sergey Yekhanin, Redmond, WA (US); Miklos Racz, New York, NY (US); Konstantin Makarychev, Chicago, IL (US); Cyrus A. Rashtchian, San Diego, CA (US); Karin Strauss, Seattle, WA (US); Bichlien Hoang Nguyen, Seattle, WA (US)

(73) Assignee: MICROSOFT TECHNOLOGY LICENSING, LLC, Redmond, WA (US)

( * ) Notice: Subject to any disclaimer, the term of this patent is extended or adjusted under 35 U.S.C. 154(b) by 998 days.

(21) Appl. No.: 16/435,400

(22) Filed: Jun. 7, 2019

(65) Prior Publication Data
US 2020/0388351 A1 Dec. 10, 2020

(51) Int. Cl.
*G01N 33/48* (2006.01)
*G16B 30/20* (2019.01)
*G16B 50/00* (2019.01)
*B01J 19/00* (2006.01)

(52) U.S. Cl.
CPC .......... *G16B 30/20* (2019.02); *B01J 19/0046* (2013.01); *G16B 50/00* (2019.02); *B01J 2219/00695* (2013.01); *B01J 2219/00698* (2013.01); *B01J 2219/00702* (2013.01); *B01J 2219/00722* (2013.01)

(58) Field of Classification Search
None
See application file for complete search history.

(56) References Cited

U.S. PATENT DOCUMENTS

2003/0220828 A1* 11/2003 Hwang .................... C08F 2/00
700/197

FOREIGN PATENT DOCUMENTS

WO     2018132457 A1     7/2018

OTHER PUBLICATIONS

Anavy, et al., "Data Storage in DNA with Fewer Synthesis Cycles using Composite DNA Letters", In Journal of Nature Biotechnology, vol. 37, Issue 10, Oct. 2019, pp. 1229-1236.
Ceze, et al., "Molecular Digital Data Storage using DNA", In Journal of Nature Reviews Genetics, vol. 20, Issue 8, Aug. 2019, 11 Pages.
"International Search Report and Written Opinion Issued in PCT Application No. PCT/US2020/035795", dated Sep. 21, 2020, 13 Pages.
Yazdi, et al., "DNA-Based Storage: Trends and Methods", In IEEE Transactions on Molecular, Biological and Multi-Scale Communications, vol. 1, Issue 3, Sep. 1, 2015, pp. 230-248.
"Notice of Allowance Issued in European Patent Application No. 20760631.0", dated Dec. 14, 2022, 7 Pages.
"Notice of Allowance Issued in European Patent Application No. 20760631.0", dated Mar. 10, 2023, 2 Pages.

* cited by examiner

*Primary Examiner* — Anna Skibinsky
(74) *Attorney, Agent, or Firm* — Benjamin Keim; Newport IP, LLC

(57) ABSTRACT

The efficiency of polymer synthesis is increased by reducing the number of monomer addition cycles needed to create a set of polymer strands. The number of cycles depends on the sequences of the polymer strands and the order in which each type of monomer is made available for addition to the growing strands. Efficiencies are created by grouping the polymer strands into batches such that all the strands in a batch require a similar number of cycles to synthesize. Efficiencies are also created by selecting an order in which the monomers are made available for addition to the growing polymer strands in a batch. Both techniques can be used together. With these techniques, the number of cycles of monomer addition and commensurate reagent use may be reduced by over 10% as compared to naïve synthesis techniques.

20 Claims, 15 Drawing Sheets

300

|  | Representative Reference Sequences 302 | Equivalent Reference Sequences 304 | | |
|---|---|---|---|---|
| 306 → | ACGT | CGTA | GTAC | TACG |
| 308 → | TGCA | GCAT | CATG | ATGC |
| 310 → | CAGT | AGTC | GTCA | TCAG |
| 312 → | TGAC | GACT | ACTG | CTGA |
| 314 → | CGAT | GATC | ATCG | TCGA |
| 316 → | TAGC | AGCT | GCTA | CTAG |

*FIG. 3*

EFFICIENT POLYMER SYNTHESIS

BACKGROUND

Polymers such as deoxyribose nucleic acid (DNA) may be used to store digital data in the sequence of monomer subunits (e.g., nucleotides). Techniques for artificially synthesizing polymers sequentially join monomer subunits to build polymeric molecules. Control of the sequence in which monomer subunits are added allows for the synthesis of polymers with specific sequences. However, synthesis of polymers—including use of oligonucleotide synthesizers to make synthetic DNA molecules—is typically performed with little or no optimization. This can waste time and reagents.

Many applications for synthetic DNA molecules such as basic research or personalized medicine operate on a small-scale. The number of DNA molecules used for a project may be equal or less than the capacity of a single oligonucleotide synthesizer. Thus, problems related to the efficiency of large-scale DNA synthesis does not arise in conventional biotechnology. However, other applications, including but not limited to using DNA to store digital data, may operate on a much larger scale that greatly exceeds the capacity of a single oligonucleotide synthesizer. Techniques for efficient polymer synthesis that save time and reduce reagent consumption are especially desirable for large-scale DNA synthesis projects.

SUMMARY

This disclosure provides techniques for structuring the usage of polymer synthesizers, such as oligonucleotide synthesizers, in ways that reduce the number of rounds of monomer addition needed to create a set of polymers. In usage scenarios discussed herein, the number of polymer strands synthesized may exceed the capacity of a synthesizer by a factor of 10, 100, 1000, or more. Thus, the way in which the polymer strands are grouped together into batches for synthesis is one variable that can be manipulated to increase efficiency.

Polymer synthesis generally proceeds by a series of rounds of monomer addition in which a single monomer, such as a nucleoside, is available for incorporation by every polymer in a batch. The available monomer is incorporated into some of the growing polymer strands depending on the intended sequences of those polymer strands. Unincorporated monomers become waste. This cycle of adding a single type of monomer is repeated with different monomers until synthesis of all the polymer strands is complete. Using DNA as an example, the available monomers may be nucleoside triphosphates (dNTPs) having one of the bases cytosine (C), guanine (G), adenine (A), or thymine (T). Nucleoside as used herein includes all structures that include nucleosides such as, but not limited to, nucleotides, nucleoside diphosphates, dNTPs, and nucleoside phosphoramidites.

A second variable that may be manipulated is the order in which the synthesizer provides the monomers for incorporation into the growing polymer strands. For example, when synthesizing DNA, the oligonucleotide synthesizer may first provide monomers corresponding to the nucleoside bases represented by A, then C, then G, and finally T before repeating the sequence and once again providing an A. Other orderings are also possible such as first G, then T, then A, and finally C. Both the grouping of polymer strands into batches and the order in which monomers are provided by the synthesizer may be controlled in tandem to increase the efficiency of polymer synthesis even more than using either technique alone.

Synthesis begins with data that represents sequences of a set of polymers to be synthesized. This data may be provided by manual input from a user or by reading a file that contains strings of data representing the intended sequences of the polymers. Each individual polymer strand has a pre-determined and specific monomer sequences that may, or may not, be unique within the set of polymers. The sequences, lengths, and type of the polymer will vary based on the intended use of the polymers such as for digital data storage, genetic screening, nanoengineering, etc.

As mentioned above, the size of the set of polymer strands may require that it be partitioned into batches. In one implementation, the size of a batch is the same as the capacity of a synthesizer. The set of polymer strands may be partitioned into batches of polymer strands based on a cost of synthesis or simply "cost." The cost is the minimum number of steps of monomer addition required to synthesize a polymer strand. Partitioning may place polymer strands with similar costs in the same "cost-grouped batch." Thus, each time the synthesizer is operated to synthesize a batch of polymers, all the polymers in the batch will have costs that are similar to each other. Batching the polymers in this way reduces the total number of steps of monomer addition needed to synthesize the entire set of polymer strands as compared to naïvely synthesizing the set of polymers without deliberate batching (e.g., arbitrarily assigning strands to batches).

Costs for synthesizing individual ones of the polymer strands may also be calculated for multiple different sequences of monomer addition. For DNA, the synthesizer may provide nucleoside monomers, for example, in an A-C-G-T or in a T-G-C-A order that is repeated until synthesis of all DNA strands is complete. The order in which the synthesizer provides monomers for addition to the strands is referred to as a "reference sequence." The particular reference sequence, or strands, used to synthesize a batch of polymers is controllable and may be different for different batches. The cost may be calculated in silico for synthesizing each polymer strand with each of the available reference sequences. This can identify which reference sequence provides the lowest-cost synthesis for each of the polymer strands. The polymer strands may be assigned to be synthesized using the respective cost-minimizing reference sequence. All of the polymer strands that are assigned to the same reference sequence, a "reference-sequence group," may then be grouped into batches based on the cost of synthesis.

After identifying an efficient process for synthesizing a set of polymer strands, data describing this process is provided to a synthesizer. The data may identify the sequences of the individual polymer strands, how the polymer strands are grouped into batches, and the order of monomer addition to be used for individual ones of the batches. One or more synthesizers manufacture the polymer strands according to the provided data thereby reducing the number of rounds of monomer addition and saving time, electricity, and chemical reagents as compared to a naïve technique for polymer synthesis.

This Summary is provided to introduce a selection of concepts in a simplified form that are further described below in the Detailed Description. This Summary is not intended to identify key features or essential features of the claimed subject matter nor is it intended to be used to limit the scope of the claimed subject matter. The term "techniques," for instance, may refer to system(s) and/or method(s) as permitted by the context described above and throughout the document.

BRIEF DESCRIPTION OF THE DRAWINGS

The Detailed Description is set forth with reference to the accompanying figures. In the figures, the left-most digit(s) of a reference number identifies the figure in which the reference number first appears. The use of the same reference numbers in different figures indicates similar or identical items.

FIG. 3 shows examples of reference sequences for synthesizing DNA.

DETAILED DESCRIPTION

This disclosure provides techniques for efficient synthesis of polymeric molecules that may incorporate an arbitrary ordering of monomer subunits. Polymeric molecules ("polymers") as used herein include any type of polymer such as biological molecules and artificial polymers. Polymeric molecules that are based on or derived from biological molecules include DNA, ribonucleic acid (RNA), and proteins. Examples of artificial polymers that may incorporate an arbitrary order of monomer subunits include xeno nucleic acids which are synthetic nucleic acid analogs that have a different sugar backbone than the natural nucleic acids DNA and RNA.

The examples and discussion provided in this disclosure are primarily directed to polynucleotides and specifically to DNA. However, the scope of this disclosure and the following claims are not limited to polynucleotides or DNA and persons of ordinary skill in the art will readily understand how to adapt the principles of synthesis design provided herein to other polymeric molecules and synthesis techniques. Polynucleotides, also referred to as oligonucleotides, as used herein refers to polymer strands of both DNA, RNA, and hybrid DNA-RNA molecules. DNA strands may include nucleotides with one of the four natural bases cytosine (C), guanine (G), adenine (A), or thymine (T), may use less than all four of the natural bases, and may additionally include one or more unnatural bases, noncanonical bases, and/or modified bases. RNA strands may include nucleotides with one of the four natural bases cytosine, guanine, adenine, or uracil (U), may use less than all four of the natural bases, and may additionally include one or more unnatural bases, noncanonical bases, and/or modified bases.

Polymer synthesis is described herein in terms of oligonucleotide synthesis using the nucleoside phosphoramidite method. However, this disclosure is not limited to only oligonucleotide synthesis using the phosphoramidite method or to only current techniques for synthesizing oligonucleotides but also encompasses other types of synthetic techniques that sequentially add specific monomer subunits to growing polymer chains.

Figure 1:
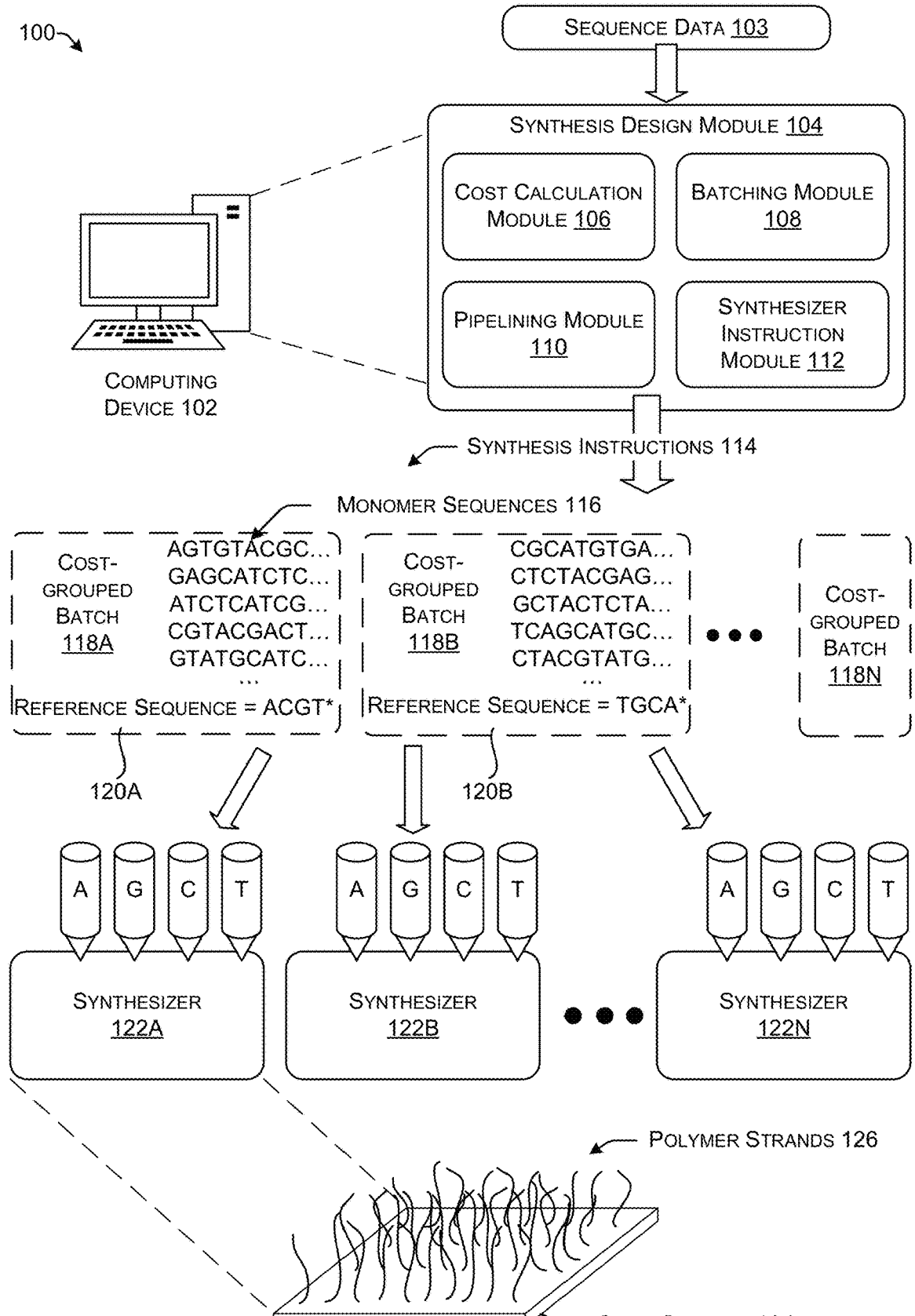
FIG. 1 is an architecture of a system for controlling polymer synthesizers using batches and reference sequences to increase the efficiency of polymer synthesis.

FIG. 1 shows an illustrative architecture 100 for efficient synthesis of polymers. A computing device 102 provides sequence data 103 indicating the sequences of the polymers to be synthesized. The computing device 102 may be any type of conventional electronic computing device such as a personal computer, laptop computer, a server, or the like. The computing device 102 may be implemented as a collection of physically separate computing devices distributed across multiple different physical locations such as a "cloud computing" implementation.

One application for synthetic polymers such as DNA is the storage of digital data. DNA data storage uses pools of synthetic oligonucleotides to encode digital data from computer files. The sequence of nucleotides on strands of DNA encode the zeros and ones representing digital data. There are various encoding schemes that may be used to convert a sequence of 0 and 1 to a sequence of A, C, G, and T. Examples of encoding schemes for storing digital data in DNA are described in Organick, et al., *Random access in large-scale DNA data storage.* 36(3) Nature Biotechnology 242 (2018). Some encoding schemes use a random seed or other technique to convert the digital data into a series of nucleotides with a pseudorandom order. Pseudorandom orderings (and true random sequences) appear statistically random because the sequences contain no recognizable patterns or irregularities. DNA strands with pseudorandom sequences contain about 25% of each nucleotide and provide some advantages for other aspects of using DNA as a medium for digital data storage. However, DNA strands encoding digital data that exhibit statistical randomness are not truly random because the DNA strands encode nonrandom digital data. Encoding schemes may be configured to create sequences of nucleotides that exclude (or allow) homopolymers. Homopolymers are repeats of the same nucleotide (e.g., -AA- or -CCC-).

Use of DNA for storing digital data may involve synthesizing a very large number of DNA strands to store terabytes, petabytes, or larger volumes of data. For example, hundreds of thousands, millions, or billions of individual DNA strands of lengths from about 100 to about 200 base pairs may be used to store collections of digital data. Synthesizing these large numbers of DNA strands can exceed the capacity of an oligonucleotide synthesizer. Thus, the synthesis may be divided into separate batches that are synthesized separately. Additionally, when synthesizing DNA at this scale, any improvement in efficiency can provide significant benefits in terms of time, electricity consumption, and the use of reagents.

The computing device 102 may include a synthesis design module 104. The synthesis design module 104 analyzes the desired sequences of the polymers to be synthesized and determines an efficient technique controlling the actual synthesizers that will produce the polymers. The synthesis design module 104 may include one or more modules such as, but are not limited to, a cost calculation module 106, a batching module 108, and a pipeline module 110, and a synthesizer instruction module 112. The time or the number of steps required to print a batch of polymer strands depends on the batch itself and on the reference sequence chosen for the batch. Factors that control the efficiency of synthesis include selection of the optimal reference sequence and selection of the optimal partitioning into batches and optimal reference sequence for each batch.

The cost calculation module 106 may determine the cost of synthesis for individual polymer strands and groups of polymer strands. Cost, as used herein, refers to the number of cycles of monomer addition that is needed to synthesize all of the polymer strands in a given batch. Synthesis of a batch is not complete until the last polymer strand in the batch is synthesized, so the cost of a batch is the same as the cost of the most expensive polymer strand in that batch. For example, consider an oligonucleotide synthesizer that repeatedly provides the monomers A, C, G, and T in that order. Synthesizing a DNA strand with the sequence ACAC will have a cost of six because the oligonucleotide synthesizer will have to cycle through the addition of A-C-G-T-A-C to add the specified nucleotides in order. The G and T provided in third and fourth cycles may be wasted or may be incorporated into a different DNA strand. In this same synthesis, a DNA strand with the sequence TTTT will have a cost of 16 because the oligonucleotide synthesizer will have to cycle through the addition of A-G-C-T four times to provide four T monomers.

The batching module 108 divides the set of polymers to be synthesized into two or more batches. The size of a batch is equal to the capacity of a polynucleotide synthesizer. As used herein, the concept of "equal" for the capacity of a synthesizer accounts for minor variations from the theoretical maximum, and thus, includes 95% or more the sequencer's maximum capacity. A polymer synthesizer has a maximum number of unique polymer sequences that it can construct during a single synthesis run. This maximum number is determined by the size and design of the synthesizer. For example, a polymer synthesizer may have a single-run capacity of, for example, 96, 384, 1000, 10,000, 30,000, 60,000, 90,000, 100,000, or more.

The set of polymer strands may be divided into batches based on a characteristic of the individual polymer strands such as cost. Thus, if the capacity of the synthesizer is 1000 strands, then the 1000 least-expensive strands to synthesize are grouped into the first batch, the next 1000 least-expensive strands are grouped into the second batch and so forth.

The pipelining module 110 divides the capacity of a synthesizer to create two or more sets of polymers simultaneously but with different starting and completion times. For example, half of the capacity of a synthesizer may be used to start synthesizing a first set of polymers while the other half of the capacity of the synthesizer is still part-way through synthesizing a second set of polymers. The pipelining module 110 may schedule the order of polymer strands to be synthesized at a given location on the synthesizer (e.g., a well in which the synthesis reaction occurs, a location on a solid substrate, etc.). This ordering of polymer strands to be synthesized at the same location may be referred to as a "pipeline."

The synthesizer instruction module 112 processes the results of the synthesis design module 104 into one or more sets of synthesis instructions 114. The synthesis instructions 114 instruct one or more synthesizers how to create the set of polymer strands. The synthesis instructions 114 may identify the sequences of the polymer strands to be included in each batch and may also identify the order of monomer addition to be used while synthesizing a given batch. The synthesis instructions 114 may be formatted into any file type or data structure suitable for a particular model of polymer synthesizer.

The synthesis instructions 114, when implemented by one or more synthesizers, minimize the synthesis time of a set of polymer strands. The synthesis instructions 114 include the monomer sequences 116 for each of the polymer strands in the set of polymer strands to be synthesized. Individual ones of the monomer sequences 116 are grouped together into batches. The batches may be cost-grouped batches 118 in which the monomer sequences 116 with similar synthesis costs are grouped together. There may be hundreds or thousands of separate cost-grouped batches 118A-118N for a given set of polymer strands.

The same reference sequence 120 may be used for every batch or the reference sequence 120A used for a first cost-grouped batch 118 a may be different than the reference sequence 120B used for a second cost-grouped batch 118B. The reference sequence 120 is the same length as the number of cycles required to synthesize all of the polymer strands in a given batch. For example, if 300 cycles of monomer addition are required to synthesize a batch, then the reference sequence 120 is 300 characters long. Most reference sequences 120 include repeating sequences caused by cycling through each of the four nucleotides used to synthesize DNA in turn. For example, the reference sequence 120A may add the nucleotides A-C-G-T in that order repeating until synthesis is complete. The repeating nature of the reference sequence 120 may be indicated by use of an asterisk so (ACGT)* stands for A-C-G-T repeated many times. Thus, "reference sequence" as used herein can refer to the shortest repeated subsequence in a reference sequence rather than the full length needed to synthesize all polymer strands in a batch.

The monomer sequences 116 in a cost-grouped batch 118 and the associated reference sequence 120 is be assigned to a synthesizer 122. If there is a single synthesizer 122, each of the cost-grouped batches 118A-118N is processed in series. In some implementations, there may be multiple synthesizers 122A, 122B, . . . , 122N that are available to process two or more batches 118 simultaneously.

Techniques for synthesizing polymers may create the polymers in solution or attached to a solid support 124 (i.e., solid-phase synthesis). Examples of solid supports 124 include beads and two-dimensional substrates. Beads may be formed from silicon, glass, polystyrene, polymeric resins, latex, etc. Two-dimensional substrates may be formed from silicon chips, glass, an insoluble polymer, or other material. A glass substrate may be formed from controlled porous glass (CPG) with pore sizes between about 50 and 300 nm. Silica substrates have a relatively homogeneous chemical surface which may be modified using well-developed silanization chemistry.

One type of polymer synthesis is synthesis of oligonucleotides such as DNA. Currently, de novo synthesis of oligonucleotides is most commonly implemented as solid-phase synthesis using the phosphoramidite method which combines phosphoramidite building blocks in the presence of a tetrazole catalyst. Nucleoside phosphoramidites are derivatives of natural or synthetic nucleosides. A phosphoramidite is a normal nucleotide with protecting groups, such as a trityl group, added to its reactive amine, hydroxyl, and phosphate groups. These protecting groups prevent unwanted side reactions and force the formation of the desired product during synthesis. Synthesis begins with a single phosphoramidite tethered to the solid support 124 by a linker.

The phosphoramidite method for synthesizing oligonucleotides with the natural bases uses a cycle of four different chemistry mixtures (i.e., corresponding to the four natural bases of DNA) to add each individual nucleoside in a 3' to 5' synthesis direction. First, a dimethoxytrityl (DMT)-protected nucleoside phosphoramidite that is attached to a solid support is deprotected by removal of the DMT using trichloroacetic acid (TCA) in a deblocking step. The deblocking step may be selectively applied to only those DNA strands for which the next nucleoside is to be added. This reveals a free 5'-hydroxyl group. Second, in an activation step, a new DMT-protected phosphoramidite is coupled to the 5'-hydroxyl group of the growing oligonucleotide chain to form a phosphite triester. Third, a capping step acetylates any remaining unreacted 5' hydroxyl groups, making the unreacted oligonucleotide chains inert to further nucleoside additions and preventing one source of base deletions. Capping is accomplished by adding an acetylating reagent composed of acetic anhydride and N-methyl imidazole. This reagent reacts only with free hydroxyl groups to irreversibly cap the oligonucleotides in which coupling failed. Fourth, an iodine oxidation converts the phosphite to a phosphate, producing a cyanoethyl-protected phosphate backbone stabilizing the phosphate linkage between the monomers in the growing oligonucleotide chain (i.e., the polymer strands 126). The DMT protecting group is removed to allow the cycle to continue and add the next nucleoside which may be the same or different than the previously added nucleoside.

After synthesis is complete, all the protecting groups are removed and the single-stranded oligonucleotides are cleaved from the solid support 124. Due to incorporation errors that occur during synthesis, the current practical limit for accurately synthesizing a DNA strand with the desired sequence is approximately 300 nucleotides.

Returning now to the synthesis design module 104, the discussion below shows that if the partitioning of the polymer strands into batches is fixed, use of a reference sequence that includes each of the available monomer subunits only once (e.g., for DNA this could be a reference sequence such as (ACGT)*, (TGCA)*, etc.) is essentially the optimal reference sequence. This is true for polymer strands with or without homopolymers that have statistically random sequences (e.g., DNA strands encoding digital data using a randomizing encoding scheme).

Consider the synthesis of a set of DNA strands S that include the four natural nucleotides. The set $\mathcal{S}$ contains strands of length n in the alphabet {A, C, G, T}. First, $\mathcal{S}$ is partitioned into $\mathcal{B}_i$ batches of size at most M. The maximum number of polymer strands that can be synthesized in a single batch at one time, which equals the capacity of an oligonucleotide synthesizer, is represented by M. The oligonucleotide synthesizer starts with M empty strands representing "positions" or capacity on the synthesizer such as independent wells, columns, or locations on a chip. Empty strands are denoted by Λ. Then, during each step t of synthesis, the oligonucleotide synthesizer adds a letter $R_t \in \{A, C, G, T\}$ according to the reference sequence R to some subset of the growing DNA strands. Synthesis is complete when all strands in the set $B_i$ are manufactured. The cost of synthesis grows as a total number of steps t increases. The cost of synthesis is reduced by identifying a technique that uses the minimum number of steps to synthesize $\mathcal{S}$. Strategies for reducing the number of steps include partitioning $\mathcal{S}$ into $\mathcal{B}_i$ (i.e., "batching") and picking letters $R_t$ for each $\mathcal{B}_i$ (independently selecting reference sequences for each batch).

Consider a trivial example in which the goal is to synthesize the strands "AGCT", "GCAT", "CAGA", and "GAGC" with an oligonucleotide synthesizer in which M=2 (i.e., each batch contains at most 2 strands). The set $\mathcal{S}$ can be partitioned into $\mathcal{B}_1$={AGCT, GCAT} and $\mathcal{B}_2$={CAGA, GAGC}. The oligonucleotide synthesizer first synthesizes $B_1$. It starts with two empty strands (Λ, Λ). Then, the oligonucleotide synthesizer presents A for appending to the first strand and obtains strands (A, Λ). Next, G is presented for appending to both strands which yields (AG, G). Then, the oligonucleotide synthesizer appends nucleotides corresponding to letters C, A, and T as follows:

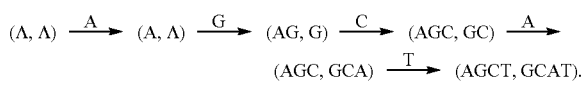

Thus, the reference sequence for $\mathcal{B}_1$ is R="AGCAT." After the last step, $\mathcal{B}_1$=(AGCT, GCAT).

The oligonucleotide synthesizer then synthesizes $B_2$ as follows:

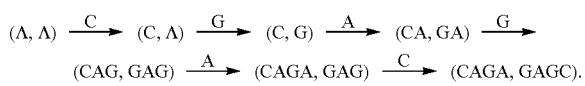

The reference sequence for $\mathcal{B}_2$ is R="CGAGAC." In this example, the oligonucleotide synthesizer would be able to create the set $\mathcal{B}_1$ in 5 steps and the set $\mathcal{B}_2$ in 6 steps. The total number of steps for synthesizing $\mathcal{S}$ is thus 11.

The oligonucleotide synthesizer will finish synthesizing all strands from $\mathcal{B}_i$ in T steps if and only if the corresponding reference sequence R is a common supersequence of all strands in $\mathcal{B}_i$. Note that in this example, "AGCAT" is a common supersequence of the strands "AGCT" and "GCAT"; "CGAGAC" is a common supersequence of the strands "CAGA" and "GAGC". Thus, finding the best common supersequence for a batch $\mathcal{B}_i$ requires finding the shortest common supersequence of the set of strands $\mathcal{B}_i$. The shortest common supersequence of two sequences X and Y is the shortest sequence which has X and Y as subsequences. This is an NP (non-deterministic polynomial-time) hard problem. The number of steps required to print all strands from a batch $\mathcal{B}$ is referred to as the cost of $\mathcal{B}$ and is denoted by cost($\mathcal{B}$). The cost of $\mathcal{B}$ equals the length of the shortest common supersequence for $\mathcal{B}$.

A simple upper bound on the cost of $\mathcal{B}$ that works for every (not only statistically random sequences) set $\mathcal{B}$ is shown using the theorems 1 and 2 below. The upper bound is different for strands that include homopolymers than for strands that do not. A strand does not contain k-homopolymers if it does not contain sub strings $$x^{k+1} = \underbrace{x \ldots x}_{k+1},$$

where x is a letter from the alphabet {A, C, G, T}. All strands of length n not containing k-homopolymers are denoted by $H_{n,k}$. The set of all strands of length n is indicated by $H_{n,\infty}$. This includes strands in which the same monomer is repeated the entire length n. With this nomenclature, $H_{n,1} \subset H_{n,2} \subset \ldots \subset H_{n,\infty}$. Strands without 1-homopolymers (e.g., AA, TT, GG, CC) are simply referred to as strands without homopolymers (i.e., k=1 is understood). Bounding the length of allowable homopolymers, such as homopolymers of up to length two, length three, etc., may be referred to as bounded homopolymers.

Theorem 1.

(1) For every $\mathcal{B} \subset H_{n,\infty}$, the cost($\mathcal{B}$)≤4n.

(2) For every $\mathcal{B} \subset H_{n,k}$, the cost($\mathcal{B}$)≤(4−1/k)(n−1)+4.

(3) The bound in (1) is tight: Specifically, cost({$A^n$, $C^n$, $G^n$, $T^n$})=4n.

Bounds for a random subset of $H_{n,l}$ of size m are shown below.

Theorem 2. The median cost of the random subset B is denoted by Median(cost($\mathcal{B}$)) (i.e., Median(cost($\mathcal{B}$)) is the number such that Pr(cost($\mathcal{B}$≤Median(cost($\mathcal{B}$)))=½).

(I) For a random subset $\mathcal{B} \subset H_{n,l}$ (i.e., without homopolymers) of size M, the Median(cost($\mathcal{B}$))≤2.2n+2 ln(2M)+1.

(II) For a random subset $\mathcal{B} \subset H_{n,\infty}$ (i.e., with homopolymers of any length) of size M, the Median(cost($\mathcal{B}$))≤2.75n+3 ln(2M).

The bounds I and II can be slightly generalized: cost(B)≤$T_\eta$ with probability 1−η, where $T_\eta$=2.2n+2 ln(M/η)+1 if B is a random subset of $H_{n,1}$ (i.e., without homopolymers), and $T_\eta$=2.75n+3 ln(2M) if B is a random subset of $H_{n,\infty}$ (i.e., with homopolymers of any length). Strands in the random subset B are chosen with repetitions. However, if M<<3n, the probability that B contains two copies of the same DNA strand are negligible.

The upper bounds on the median number of steps required to manufacture M random strands for some values of M are shown in Table 1 below. All of the DNA strands are of length 100 and use only the four canonical nucleotides. These values fall within the standard deviation ranges of the values obtained for the experimental results of in silico synthesis shown below in Table 3.

TABLE 1

Upper bounds on the median number of steps required to manufacture DNA strands having a random sequence.

| Strand count $|\mathcal{B}|$ | cost ($\mathcal{B}$) without homopolymers | cost ($\mathcal{B}$) with homopolymers |
|---|---|---|
| 500,000 | 248 | 317 |
| 1,000,000 | 249 | 319 |
| 2,000,000 | 251 | 321 |
| 4,000,000 | 252 | 323 |

In the following discussion of establishing the desired upper and lower bounds, R refers to a given reference sequence and S refers to a given DNA strand. The problem to be solved can be formulated as determining whether R=$R_1 \ldots R_T$ can be used to synthesize the strand S. Let $\tau_i$(R, S) be the step at which the oligonucleotide synthesizer adds the i-th character of S (denoted $S_i$) given the reference sequence R. If the oligonucleotide synthesizer cannot make the entire strand $S$ using R and so it does not add the i-th character, then $\tau_i$(R, S) is T+1. To test whether it is possible to make $S$ using R, $\tau_n$(R, S) is compared with T: If $\tau_n$(R, S)≤T, then it is possible to make S using R; otherwise, it is not possible.

Let $X_i$(R, S)=$\tau_i$(R, S)−$\tau_{i-1}$(R, S) for i>1 and $X_1$(R, S)=$\tau_1$(R, S). Each variable $X_i$ (R, S) equals to the number of characters in the reference sequence the oligonucleotide synthesizer advances through to synthesize the i-th character of S. $X_i$(R, S) is referred to here as "steps." This may also be thought of as rounds of monomer addition. In terms of the steps, the criterion for synthesizing S can be stated as follows: it is possible to synthesize S using R if and only if $$\tau_n(R, S) = \sum_i X_i(R, S) \leq T.$$

If the strand S is statistically random, then $X_i$(R, S) is a random variable, so the question of whether S can be synthesized using R reduces to analyzing a stochastic process. To show that cost($\mathcal{B}$)≤T*, it must be proved that there exists a reference sequence R such that $$\max_{S \in \mathcal{B}} \sum_i X_i(R, S) \leq T^*$$

with high probability. To show that Median(cost($\mathcal{B}$))≤T*, it is necessary to prove that there exists a reference sequence R such that $$Pr\left(\max_{S \in \mathcal{B}} \sum_i X_i(R, S) \leq T^*\right) \geq 1/2.$$

On the other hand, to show that Median(cost($\mathcal{B}$))>T*, it is necessary to prove that $$Pr\left(\min_R \max_{S \in \mathcal{B}} \sum_i X_i(R, S) > T^*\right) > 1/2.$$

The same reference sequence, (ACGT)*, is used to prove all upper bounds. The lengths of the strand R are equal to the desired upper bounds from Theorems 1 and 2.

For the reference sequence $(ACGT)^n$ and $(ACGT)^*$, the following items are true:

Item (1): the oligonucleotide synthesizer will use the i-th quad ACGT in the reference sequence $(ACGT)^n$ to print the i-th letter in S. The length of the reference sequence $(ACGT)^n$ is 4n.

Item (2): For k=1, consider jumps $X_i(R, S)$ from the previous section for a strand S without homopolymers. The length of every jump $X_i(R, S)$, except for the first jump $X_1(R, S)$, is at most three, because the distance between the t-th letter in R and the next occurrence of any letter other than $R_t$ in R is 1, 2, or 3. Hence, $\Sigma_i X_i(R, S) \leq 3n+1$ (the first jump $X_1$ is 1, 2, 3, or 4) for every S. This shows that $cost(H_{n,1}) \leq 3n+1$.

Item (3): Showing that the bound cost({An, Cn, Gn, Tn})≥4n is almost trivial: The reference sequence R should contain n characters A, n characters C, n characters G, and n characters T to print strands An, Cn, Gn, Tn. Hence, the length of R is at least 4n.

To prove that $$Pr\left(\max_{s \in \mathcal{B}} \sum_i X_i(R, S) \leq T^*\right) \geq \frac{1}{2},$$

where $T^* = 2.2n + 2 \ln(2M) + 1$ for item (1) and $T^* = 2.75n + 3 \ln(2M)$ for item (2). By the union bound, it is sufficient to show that for a sequence of a polymer strand S with random ordering of monomers:

$$Pr\left(\sum_i X_i(R, S) > T^*\right) \leq \frac{1}{2M}.$$

Consider a random sequence representing a polymer strand S with homopolymers. S can be generated by the Markov chain with states {A, C, G, T} and transition probabilities ¼ between every two states. Observe that no matter what the current state is the next state is going to be at distance 1, 2, 3, or 4 from the current position in the reference sequence with probability ¼ each (the reference sequence is $(ACGT)^*$). Hence, the random variables $X_i(R,S)$ are independent and identically distributed (i.i.d.) random variables uniformly distributed in {1, 2, 3, 4}.

Similarly, for a random strand S without homopolymers every jump $X_i(R, S)$ (i>1) is a uniform random number in {1, 2, 3}. This happens because random strands without homopolymers can be generated by the Markov chain with states {A, C, G, T} and transition probabilities ⅓ between every two distinct states (i.e., this is a Markov chain on the complete graph without self-loops). The distance in the reference sequence between one state and the next state can be 1, 2, or 3. The desired results are obtained by applying Lemma 1 with k=3 and η=1/(2M) in item (1); and k=4 and η=1/(2M) in item (2).

Lemma 1: Let $X_1, \ldots, X_n$ be a sequence of i.i.d. random variables. Suppose that each $X_i$ is uniformly distributed in the set $\{1, \ldots, k\}$. Then, for every η>0, $$Pr\left(\sum_i X_i \geq 0.55(k+1)n + (k-1)\ln(1/\eta)\right) \leq \eta.$$

This is proved using the following inequality (1):

$$Pr\left(\sum_i X_i \geq \mu n + t\right) \leq \exp\left(\frac{n\sigma^2}{b^2}((1+\varepsilon)\ln(1+\varepsilon) - \varepsilon)\right),$$

where $\mu = EX_i$, $\sigma^2 = Var[X_i]$, $\varepsilon = (n\sigma^2)$, and b is an upper bound on $X_i - \mu$ (i.e., $X_i - \mu \leq b$ almost surely). Observe that $$(1+\varepsilon)\ln(1+\varepsilon) - \varepsilon \geq \frac{\varepsilon}{2} - 0.15.$$

Thus, the above inequality (1) implies:

$$Pr\left(\sum_i X_i \geq \mu n + t\right) \leq \exp\left(-\frac{n\sigma^2}{b^2}((1+\varepsilon)\ln(1+\varepsilon) - \varepsilon)\right)$$

$$\leq \exp\left(-\frac{n\sigma^2}{b^2}(\varepsilon/2 - 0.15)\right)$$

$$= \exp\left(-\left(\frac{n\sigma^2}{b^2} \times \frac{bt}{2n\sigma^2} - \frac{0.15n\sigma^2}{b^2}\right)\right)$$

$$= \exp\left(-\frac{1}{2b}\left(t - \frac{0.3n\sigma^2}{b}\right)\right).$$

Let $$t = 2b\ln(1/\eta) + \frac{0.3n\sigma^2}{b}.$$

Then, $Pr(\Sigma_i X_i \leq \mu n + t) \leq \eta$. Computing μ, $\sigma^2$, and b to obtain an expression for t in terms of k, η, and n yields $$\mu = (k+1)/2, \quad b = k - \mu = (k-1)/2,$$
$$\sigma^2 = Var[X_i] =$$
$$EX_i^2 - (EX_i)^2 = \frac{1}{k}\sum_{j=1}^k j^2 - \left(\frac{k+1}{2}\right)^2 = \frac{(k+1)(2k+1)}{6} - \frac{(k+1)^2}{4} = \frac{k^2-1}{12},$$

and $$\frac{0.3n\sigma^2}{b} = \frac{0.3n(k^2-1)}{6(k-1)} = \frac{(k+1)n}{20}.$$

Therefore, $$t = (k-1)\ln(1/\eta) + \frac{(k+1)n}{20}.$$

Now, observe that 0.55(k+1)n+(k−1) ln(1/η)=μn+t, hence $$Pr\left(\sum_i X_i \geq 0.55(k+1)n + (k-1)\ln(1/\eta)\right) \leq \eta.$$

This shows that the approximate upper bound on the cost of synthesizing polymer strands.

Turning now to the approximate lower bound on the cost of synthesizing a random set $\mathcal{B}$ of size M. To derive these bounds, the sum of i.i.d. random variables (similar to the previous section) is approximated with a Gaussian random variable. This shows that with high probability over a random set of strands $\mathcal{B}$ no reference sequence of length T can be used to manufacture all S∈ $\mathcal{B}$. The probability that a given reference sequence R can be used to manufacture all strands in a random set $\mathcal{B}$ of size M equals $$\Pr_{\mathcal{B}}(R \text{ is good for } S \forall\, S \in \mathcal{B}) = \left(\Pr_{S}(R \text{ is good for } S)\right)^{M}.$$

The probability in the right-hand side is taken over a random strand S with or without homopolymers. Here, all strands in $\mathcal{B}$ are sampled independently. Let $$p(T) = \max_{R} \Pr_{S}(R \text{ is good for } S),$$

where the maximum is taken over all reference sequences R of length T. Thus, $$\Pr_{\mathcal{B}}(R \text{ is good for } S \forall\, S \in \mathcal{B}) = \left(\Pr_{S}(R \text{ is good for } S)\right)^{|\mathcal{B}|} \le p(T)^{M}.$$

The set of all possible reference sequences of length T is represented by $\mathcal{R}$. Note that for manufacturing strands S without homopolymers it is sufficient to consider reference sequences R without homopolymers as well. The expected number of strands R∈ $\mathcal{R}$ that are suitable for manufacturing all strands S in $\mathcal{B}$ equals $$\sum_{R \in \mathcal{R}} \Pr_{\mathcal{B}}(R \text{ is good for } S \forall\, S \in \mathcal{B}) \le |\mathcal{R}| p(T)^{M}.$$

The probability that there is a strand R in $\mathcal{R}$ that is good for all S in $\mathcal{B}$ is at most the expectation above; which, in turn, is at most $|\mathcal{R}|p(T)^{M}$. Therefore, to show that T is a lower bound on Median(cost($\mathcal{B}$)), it must be shown that $|\mathcal{R}| p(T)^{M} \le 1/2$, or, equivalently, $$p(T) \le \left(\frac{1}{2|\mathcal{R}|}\right)^{1/M}.$$

For simplicity, focusing on the lower bound for strands without homopolymers, R is good for S if $$\sum_{i} X_i(R, S) \le T.$$

For an arbitrary R, the random variables Xi(R, S) are not i.i.d.; however, the multivariate random variable X(R, S)= $(X_1(R, S), \ldots, X_n(R, S))$ is greater than the multivariate random variable Y=$(Y_1, \ldots, Y_n)$ in the usual stochastic order:

$$(X_1(R,S), \ldots, X_n(R,S)) \ge_{st} (Y_1, \ldots, Y_n),$$

where $Y_1, \ldots, Y_n$ are i.i.d. random variables uniformly distributed in {1, 2, 3}. A random variable X is greater than Y in the usual stochastic order if, for every upward closed set U, there is Pr(X∈ U)≥Pr(Y∈ U). Note that $X \ge_{st} Y$ if and only if there exist random variables $\tilde{X}$ and $\tilde{Y}$, defined on the same probability space such that $\tilde{X}$=X, $\tilde{Y}$=Y and $\tilde{X} \ge \tilde{Y}$ almost surely. Hence, Pr($\Sigma_i X_i(R,S) \ge T$)≥Pr($\Sigma_i Y_i \ge T$) and Pr($\Sigma_i X_i(R,S) \le T$)≤Pr($\Sigma_i Y_i \le T$).

The sum $\Sigma_i Y_i$ may be approximated with a Gaussian distribution with mean $\mu$=2n and variance $\sigma_2$=2n/3 (denoted by $\mathcal{N}$ (2n, 2n/3)). This yields $$p(T) = \max_{R \in \mathcal{R}} \Pr\left(\sum_i X_i(R, S) \le T\right) \le \Pr\left(\sum_i Y_i \le T\right) \approx \Pr(g \le T).$$

Here, g~$\mathcal{N}$ (2n, 2n/3). To satisfy the inequality shown in paragraph [0063] above, T is selected such that $$\Pr(g \le T) \le \left(\frac{1}{2|\mathcal{R}|}\right)^{1/M}.$$

This condition on T is equivalent to $$T \le \Phi_{2n,2n/3}^{-1}\left(\left(\frac{1}{2|\mathcal{R}|}\right)^{1/M}\right) = 2n + \sqrt{\frac{2n}{3}} \cdot \Phi_{0,1}^{-1}\left(\left(\frac{1}{2|\mathcal{R}|}\right)^{1/M}\right),$$

where $\Phi_{2n,2n/3}$ and $\Phi_{0,1}$ are cumulative distribution functions for Gaussian $\mathcal{N}$ (2n, 2n/3) and $\mathcal{N}$ (0, 1) distributions, respectively. Note that $|\mathcal{R}|=3^T$. To simplify the expression above, use of a crude upper bound $\mathcal{R} \le 3^{3n}$ obtains the following bound on T, $$T \le 2n + \sqrt{\frac{2n}{3}} \cdot \Phi_{0,1}^{-1}(3^{-3n/M}).$$

Using this formula and a similar formula for strands without homopolymers, approximate lower bounds on Median(cost($\mathcal{B}$)) are obtained as shown in Table 2 below. All of the DNA strands are of length 100 and use only the four canonical nucleotides.

TABLE 2

Approximate lower bounds on the median number of steps required to manufacture DNA strands having a random sequence.

| Strand count $|\mathcal{B}|$ | cost ($\mathcal{S}$) without homopolymers | cost ($\mathcal{S}$) with homopolymers |
|---|---|---|
| 500,000 | 227 | 285 |
| 1,000,000 | 228 | 287 |
| 2,000,000 | 230 | 289 |
| 4,000,000 | 231 | 291 |

Figure 2:
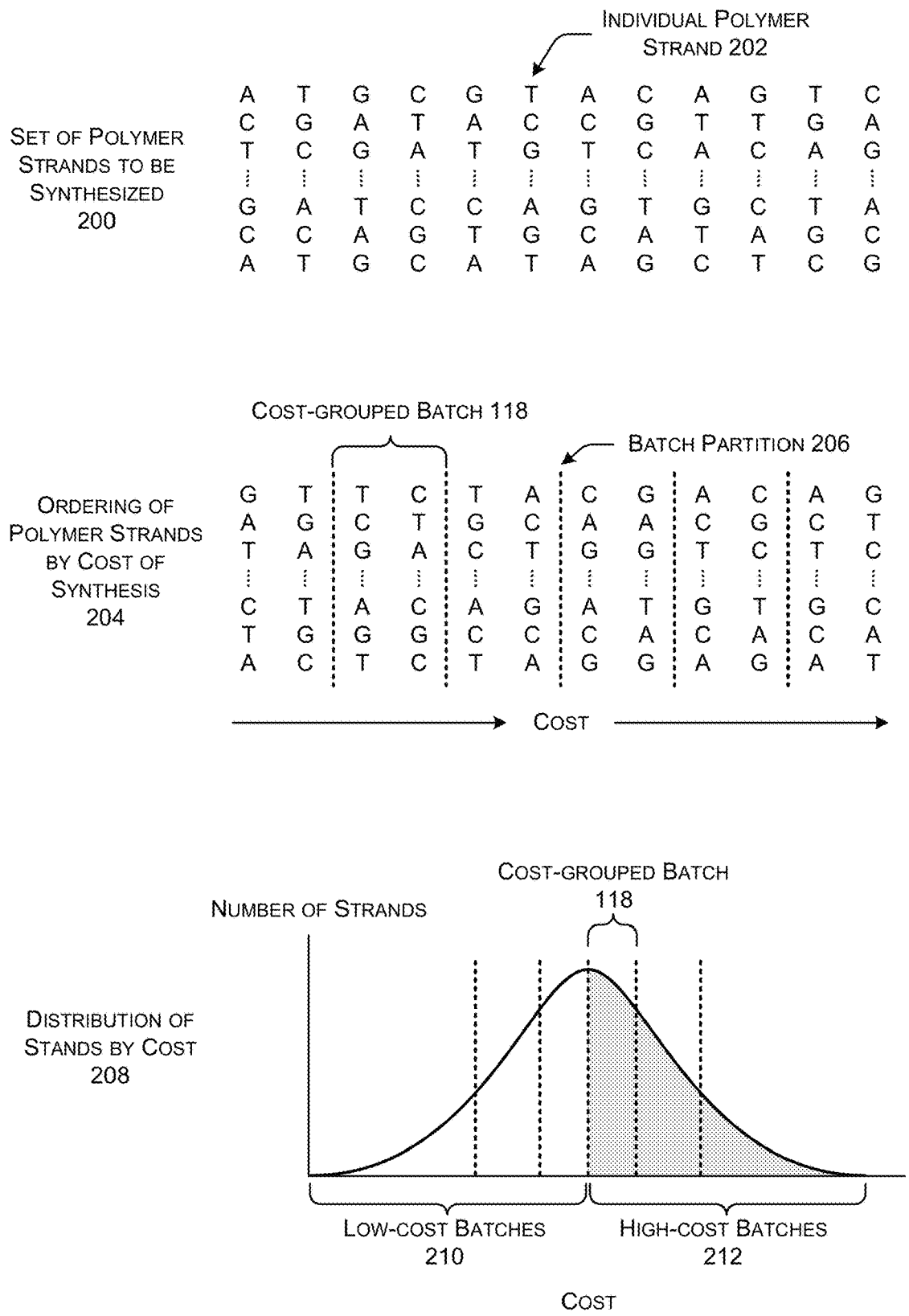
FIG. 2 illustrates ordering polymers into batches based on the cost of synthesis.

FIG. 2 shows an example of grouping polymer sequences into batches. The set of strands to be synthesized 200, represented by $\mathcal{S}$ as above, may be represented in electronic form such as a file (e.g., the sequence data 103 shown in FIG. 1) that contains strings of letters, numbers, and/or symbols which represent the monomers that make up the polymers to be synthesized. The file may be in any format of such as, a text file, a delimited text file, a hypertext mark-up language file, etc. For polynucleotides, the set of strands to be synthesized 200 may be stored in a file with a specialized format such as FASTQ, EMBL, FASTA or the like.

There may be millions or billions of individual polymer strands 202 in the set of polymer strands to be synthesized 200. Each of the individual polymer strands 202 may have a unique sequence. It is also possible for two or more to have the same sequence. All of the polymer strands 202 may have the same length n. The length for DNA strands may be, for example, between 60-300 nucleotides, between 80-220 nucleotides, or between 100-150 nucleotides.

It may be impossible for a single synthesizer to process the entire set of polymer strands in one run. The maximum number of individual polymer strands 202 that may be synthesized simultaneously by a synthesizer is at most M (i.e., the manufacturing capacity of the machine). Dividing the set of polymer strands to be synthesized 200 into cost-group batches 118 rather than arbitrarily forming batches reduces the total number of steps needed to synthesize $\mathcal{S}$ as compared to a naïve batching technique that does not consider the cost of synthesis.

In FIG. 2 the size M of a cost-grouped batch 118 is two strands as illustrated by the dotted batch partitions 206. However, in an actual implementation, the number of polymer strands in a batch may be hundreds or thousands.

Thus, one goal of batching is to identify a process for synthesizing a set of strands $\mathcal{S}$ that contains kM individual polymer strands 202 (k may be in the thousands, millions, or billions) that minimizes cost. This is achieved by partitioning $\mathcal{B}_i, \ldots, \mathcal{B}_k$ so as to minimize $\Sigma_{i=1}^{k} \text{cost}(\mathcal{B}_i)$.

One technique for minimizing the cost by creating batches splits the set $\mathcal{S}$ into $\mathcal{B}_i, \ldots, \mathcal{B}_k$ and synthesizes all the batches $\mathcal{B}_i, \ldots, \mathcal{B}_k$ using the same reference sequence R that includes each of monomer subunits once such as, for example, (ACGT)*. With this technique, for each polymer strand $S \in \mathcal{S}$ the cost of synthesizing that polymer strand $c_S = \text{cost}_{R*}(S)$.

First, the polymer strands may be ordered by the cost of synthesis 204. Thus, all polymer strands S may be sorted by $c_S$ in descending order. The ordering may simply order each of the individual polymer strands 202 from the least expensive to the most expensive according to the cost or number of steps of synthesis needed to manufacture the strand using the reference sequence selected for synthesis, for example, (ACGT)*. If any two or more of the individual polymer strands 202 have the same cost, the ordering for those strands with respect to (w.r.t.) each other may be random.

Second, the ordered set of strands $S \in \mathcal{S}$ may be divided into k batches $\mathcal{B}$. The batch partition 206 indicates a location where the ordering of polymer strands by the cost of synthesis 204 is divided into batches. The batches need not all contain exactly M strands. For example, if the total number of strands in $\mathcal{S}$ is not evenly divisible by M, then one of the batches may contain the remainder which is less M strands. Alternatively, more than one batch may contain less than its maximum capacity.

The cost of dividing into batches is estimated by:

$$\sum_{i=1}^{k} \text{cost}_{R*}(\mathcal{B}_i) = \sum_{i=1}^{k} \max_{S \in \mathcal{B}_i} \text{cost}_{R*}(S).$$

Here, $Q_\alpha(\mathcal{S})$ denotes the top $\alpha$ quantile of the set $\mathcal{S}$ (i.e., the unique $x \in \{\text{cost}_{R*}(S): S \in \mathcal{S}\}$) such that $$|\{S \in \mathcal{S}: \text{cost}_{R*}(S) \geq x\}| \geq \alpha |\mathcal{S}|;$$

$$|\{S \in \mathcal{S}: \text{cost}_{R*}(S) > x\}| \leq \alpha |\mathcal{S}|;$$

Note that $Q_0(\mathcal{S})$ is the cost of the most expensive element in $\mathcal{S}$; and $Q_1(\mathcal{S})$ is the cost of the least expensive element in $\mathcal{S}$. Observe that, because the total number of polymer strands kM divides k:

$$\max_{S \in \mathcal{B}_i} \text{cost}_{R*}(S) \leq Q_{(i-1)/k}(\mathcal{S}).$$

Hence, the cost of the partitioning is at most $$\sum_{i=1}^{k} Q_{(i-1)/k}(\mathcal{S}).$$

As described earlier, the cost $\text{cost}_{R*}(S)$ of a random strand Scan be approximated by $\mu n + g_s$, where $g_s$ is a Gaussian random variable with mean 0 and variance $\sigma^2 n$, where $\mu=2$, $\sigma^2=1/3$ for polymer strands without homopolymers; and $\mu=2.5$ and $\sigma^2=1.25$ for polymer strands with homopolymers. The Gaussian distribution is symmetric around the mean; as a consequence:

$$\frac{E[Q_\alpha(\mathcal{S}) + Q_{1-\alpha}(\mathcal{S})]}{2} = \mu n.$$

By grouping the terms $Q_{(i-1)/k}$ and $Q_{k-i+1)/k}$ together for $i>1$ in the sum immediately above the estimate of the expected cost is:

$$E\left[\sum_{i=1}^{k} Q_{(i-1)/k}(\mathcal{S})\right] =$$

$$E\left[\sum_{i=2}^{k-1} \frac{Q_{(i-1)/k}(\mathcal{S}) + Q_{(k-i+1)/k}(\mathcal{S})}{2}\right] + EQ_0(\mathcal{S}) = k\mu n + E[Q_0(\mathcal{S}) - \mu n].$$

Note that $Q_0(\mathcal{S}) - \mu n \cong \sigma\sqrt{2n\log M}$ (the expected maximum deviation from the mean). Therefore, the average cost of producing one batch of strands is approximately equal to $\mu n + (\sigma\sqrt{2n\log M})/k$. For a large number of batches k, this quantity is very close to $\mu n$.

Grouping the individual polymer strands 202 in cost-grouped batches 118 by the cost of synthesis minimizes the variation in cost between the individual polymer strands 202 in each cost-grouped batch 118. The total number of steps needed to synthesize a batch is the number of steps needed to synthesize the most expensive strand in that batch. For example, if most strands in a batch can be synthesized with the cost of approximately 350 but one strand in the batch has a cost of 500 then the cost of synthesizing the batch will be 500. By grouping the individual polymer strands 202 in batches based on similarity in cost of synthesis, synthesis of all the strands in a batch is completed at approximately the same time.

The distribution of polymer strands by cost 208 has a normal distribution (i.e., a bell curve) if the sequences of the individual polymer strands 202 are statistically random.

Most of the individual polymer strands 202 will have a cost that is near the median cost for the set of polymer strands to be synthesized 200. Thus, most of the cost-group batches 118 will also have a cost that is near the median. If there is a large number of batches, a large k, the expected average cost $$\frac{1}{k}\sum_{i=1}^{k}\text{cost}(\mathcal{B}_i)$$

tends to twice the length of the strands (2n) in sets of strands that do not include homopolymers and tends to 2.5n for strands that do include homopolymers as shown above.

The cost-grouped batches 118 with a cost of synthesis that is less than the median for the set of polymer strands to be synthesized 200 are referred to as low-cost batches 210. Those batches that cost more than the median to synthesize are referred to as high-cost batches 212. There will be a small number of strands, and batches, that have costs which are much lower than the median and which are much higher than the median representing the "long tails" of a normal distribution.

If the individual polymer strands 202 are grouped arbitrarily, first-come-first-served, etc. into batches in a way that does not consider the cost of synthesis, each batch will likely have one or more polymer strands 202 with a high cost. Thus, the cost of synthesizing every batch will be high. But if the batches are grouped by cost, all the strands with the highest costs will be grouped into the same batch. This batch, the highest of the high-cost batches 212 will take much longer than the average time to synthesize, but strands in this batch will not bring up the synthesis time of other batches. Grouping the set of polymer strands to be synthesized 200 into cost-grouped batches 118 reduces the total synthesis time as compared to naïve batching that does not consider the cost of synthesis.

Given the variation in costs for synthesizing the cost-grouped batches 118, it is possible to further reduce the number of steps needed to synthesize $S \in \mathcal{S}$ by using the reverse of the reference sequence to synthesize the high-cost batches 212. The reverse reference sequence $\overline{R}^*$ of a reference sequence $R^*$ is a reference sequence that cycles through the monomers in a reverse order. For example, for reference sequence (ACGT)* the reverse reference sequence is (TGCA)*.

The set of strands $\mathcal{S}$ is partitioned into batches $\mathcal{B}_1, \ldots, \mathcal{B}_k$ based on the cost of synthesis for $R^*$ using the process described above. However, $\overline{R}^*$ is used as the reference sequence if $\text{cost}_{R^*}(\mathcal{B}_i) > \text{cost}_{\overline{R}^*}(\mathcal{B}_i)$ (i.e., the high-cost batches 212). If $\text{cost}_{R^*}(\mathcal{B}_i) \leq \text{cost}_{\overline{R}^*}(\mathcal{B}_i)$ (i.e., the low-cost batches 210) then $R^*$ is used as the reference sequence. Thus, the cost of every batch $\mathcal{B}_i$ equals $\min(\text{cost}_{R^*}(\mathcal{B}_i), \text{cost}_{\overline{R}^*}(\mathcal{B}_i))$.

Lemma 2 below shows that for every strand S, $(\text{cost}_{R^*}(S) + \text{cost}_{\overline{R}^*}(S))/2 = \mu n$. Hence, $$\min(\text{cost}_{R^*}(S), \text{cost}_{\overline{R}^*}(S)) \leq \mu n.$$

That is, for every strand S either $\text{cost}_{R^*}(S) \leq \mu n$ or $\text{cost}_{\overline{R}^*}(S) \leq \mu n$. For example, a batch $\mathcal{B}_i$ satisfies one of the following conditions:

for all $S \in \mathcal{B}_i$, $\text{cost}_{R^*}(S) \leq \mu n$; or for all $S \in \mathcal{B}_i$, $\text{cost}_{\overline{R}^*}(S) \leq \mu n$;

then $\min(\text{cost}_{R^*}(\mathcal{B}_i), \text{cost}_{\overline{R}^*}(\mathcal{B}_i))$ Observe that there is at most one $\mathcal{B}_i$ that contains two strands S' and S" with $\text{cost}_{R^*}(S') < \mu n$ but $\text{cost}_{R^*}(S'') > \mu n$ just because $\mathcal{B}_i$'s are ordered by $\text{cost}_{R^*}(S)$ (i.e., the cost of any strand S in $\mathcal{B}_i$ is less than the cost of any strand S' in $\mathcal{B}_j$ for i>j)). Therefore, the cost of all batches but one (call it $\mathcal{B}_z$) is upper bound by $\mu n$. Accordingly, the cost of $\mathcal{B}_z$ is only slightly bigger than $\mu n$ because the sequences of the polymer strands are random. Therefore, the cost of the partitioning is at most $\mu n$ per batch (ignoring a small error term).

A slightly more careful analysis shows that for a large k the amortized cost of the partitioning is approximately equal to $(\mu n - \sqrt{2n/\pi}\sigma)$ per batch ($\sqrt{2n/\pi}\sigma$ is the expectation of the absolute value of a Gaussian random variable with mean 0 and variance $\sigma^2$). For strands without homopolymers: $\mu=2$ and $\sigma^2=2/3$. Hence, the average cost per batch is $$2n - \sqrt{\frac{4n}{3\pi}}.$$

Lemma 2. For every strand S without homopolymers of length n:

$$\text{cost}_{R^*}(S) + \text{cost}_{\overline{R}^*}(S) = \mu n.$$

This is because the cost of a strand S equals $\sum_{i=1}^{n} X_i(R^*, S)$. For the reference sequence $R^*=(ACGT)^*$, each $X_i(R^*,S)$ depends only on the characters $S_{i-1}$ and $S_i$. Specifically, $X_i(R^*, S)$ equals the distance between letters $S_{i-1}$ and $S_i$ in $R^*$. Thus, to compute the cost of the strand S w.r.t. the reference sequence $R^*$ and, similarly, w.r.t. the reference sequence $\overline{R}^*$, the costs of transitions from the letter $S_{i-1}$ to $S_i$ for $i=1, \ldots n$ are summed.

TABLE 3

Cost of transitions for reference sequence (ACGT)*.

| cost w.r.t $R^*$ | cost w.r.t $\overline{R}^*$ | Transitions $S_{i-1} \to S_i$ |
| --- | --- | --- |
| 1 | 3 | A → C, C → G, G → T, T → A |
| 2 | 2 | A → G, C → T, G → A, T → C |
| 3 | 1 | A → T, C → A, G → C, T → G |

Observe that the sum of the cost of a transition $S_{i-1} \to S_i$ w.r.t $R^*$ and the cost of the same transition w.r.t $\overline{R}^*$ equals to 4 (because $\overline{R}^*$ is reversed $R^*$; also see Table 3). Hence, $$\sum_{i=1}^{n} X_i(R^*, S) + \sum_{i=1}^{n} X_i(\overline{R}^*, S) = 4n.$$

Thus, for a given polymer strand S, the cost of synthesis using $R^*$ and $\overline{R}^*$ cannot both be large. If synthesis with a reference sequence has a high cost, then synthesis with the reverse reference sequence will have a low cost. For polymer strands with a cost that is close to 2n, the advantage of switching from a reference sequence to its reverse is small. By synthesizing the high-cost batches 212 using $\overline{R}^*$, the total cost for synthesizing $\mathcal{S}$ is the same as synthesizing two sets of the low-cost batches 210.

FIG. 3 shows an illustrative table 300 of all the possible reference sequences of length four without repeats that can be created from the canonical DNA nucleotides (i.e., alphabet-unique reference sequence permutations). Each of the reference sequences shown in the table 300 uses each one of the four standard DNA nucleotides only once. Each of the reference sequences also represents a sequence of nucleotide addition that is repeated multiple times. The sequence of nucleotide addition represented by any one of the reference sequences in the table 300 is thus repeated until all the DNA strands in a batch have been synthesized by an oligonucleotide synthesizer. Thus, the length of a reference sequence is the length of a shortest repeating unit of the strand not the total number of cycles of monomer addition needed to synthesize any strand or batch of strands.

Because each reference sequence is repeated many times during synthesis, the repeated sequence of nucleotides contains other four-nucleotide sequences within it. Consider the first row 306 of the table 300. In this row 306, the first reference sequence listed is ACGT which is referred to here as a representative reference sequence 302. Operating an oligonucleotide synthesizer according to the nucleotide addition order specified by the reference sequence ACGT will result in repeated addition of adenosine phosphoramidite, cytosine phosphoramidite, guanosine phosphoramidite, thymidine phosphoramidite, and then restart the cycle of addition with adenosine phosphoramidite. This cycle of nucleoside phosphoramidites can be represented as ACGT-ACGT-ACGT- . . . . This same sequence of nucleoside addition, with only a change in the first few nucleotides added, also results from the reference sequences CGTA, CGAC, and TACG. Thus, those reference sequences are referred to as equivalent reference sequences 304 because they lead to an equivalent cycle of nucleotide additions.

Given an alphabet of size four corresponding to the four natural nucleosides, there are six possible representative reference sequences 302 that are shown in the first column of each of the rows 306, 308, 310, 312, 314, and 316 of the table 300 in FIG. 3. Identification of the reference sequences in the first column of the table 300 as being the representative reference sequence 302 is arbitrary. The reference sequences in any column of the table 300 could be designated as the representative reference sequences 302. A feature that identifies a group of representative reference sequences 302 is that there is no shared sequence of length three within any of the six reference sequences. This relationship between the sequence of the reference sequences is evident by examination of the reference sequences in each of the columns of the table 300.

When a single reference sequence is used for the synthesis of all batches (i.e., a constant reference sequence technique) any of the representative reference sequences 302 or the equivalent reference sequences 304 may be substituted for each other. When a reference sequence and its reverse are used together any pair reference sequences from the same column of row 306 and row 308 (e.g., (ACGT)* and (TGCA)*), row 310 and row 312 (e.g., (CAGT)* and (TGAC)*), or row 314 and row 316 (e.g., (CGAT)* and (TAGC)*) may be used. If six different reference sequences are used, the representative reference sequences 302 (or any other column the table 300) may be used as the six different reference sequences.

Although the table 300 in FIG. 3 shows reference sequences for DNA nucleotides, persons of ordinary skill in the art will understand how to derive representative reference sequences 302 and equivalent reference sequences 304 for other types of polymers including those with a different number of unique monomers.

Figure 4:
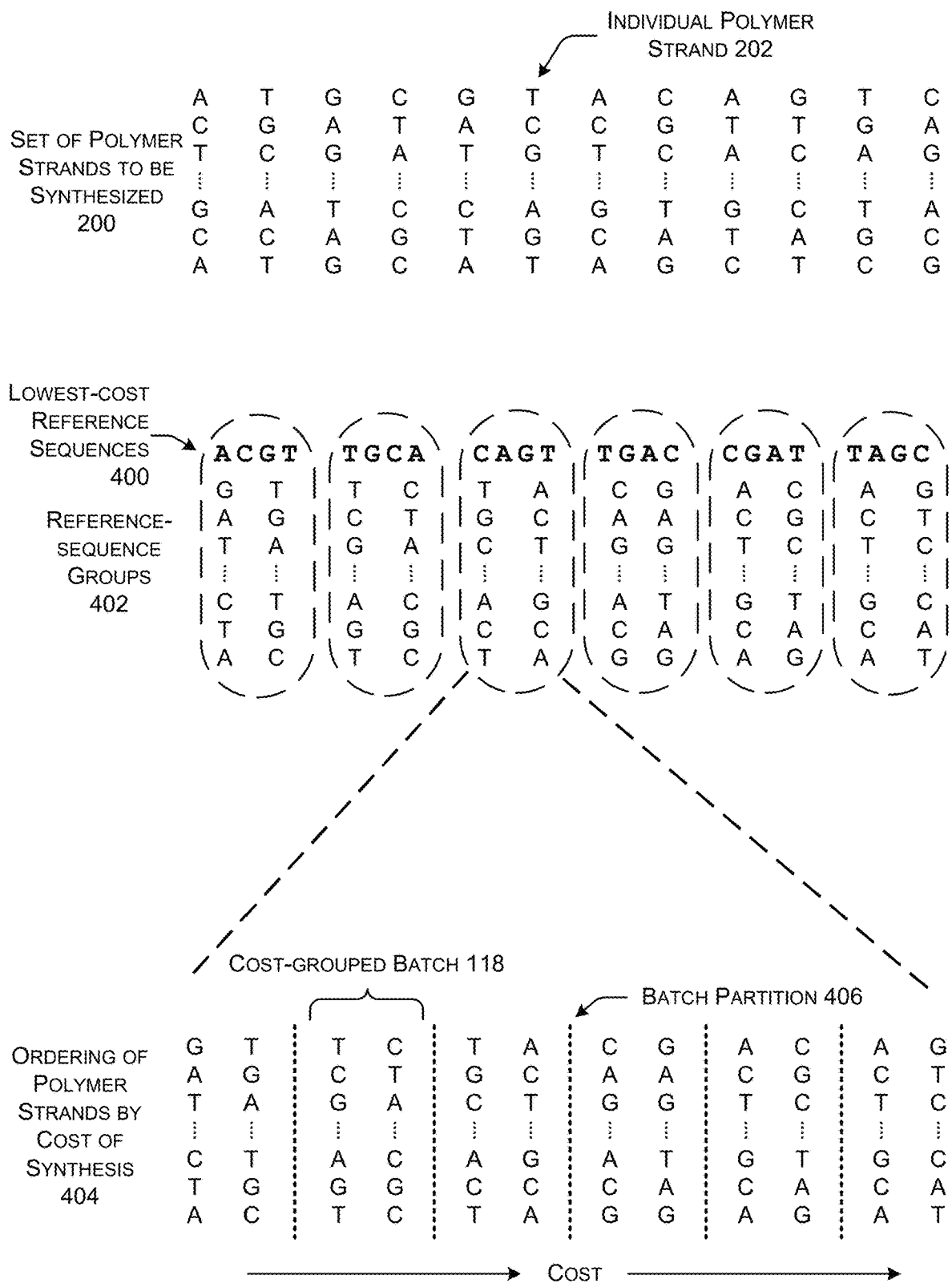
FIG. 4 illustrates grouping of polymers by the lowest-cost reference sequence and further ordering of the polymers in each reference-sequence group into batches based on the cost of synthesis.

FIG. 4 illustrates an additional technique for minimizing synthesis cost. This technique first groups individual polymer strands 202 according to the lowest-cost reference sequence 400 and then divides those reference-sequence groups 402 into cost-group batches 118 as described above. As in FIG. 3, the set of polymer strands to be synthesized 200 contains many individual polymer strands 202. Rather than using a fixed reference sequence for the synthesis of all the individual polymer strands 202, the cost of synthesis for each individual polymer strand 202 for each of a plurality of reference sequences is calculated. For DNA strands using the four canonical bases, the plurality of reference sequences may be the representative reference sequences 302: (ACGT)*, (TGCA)*, (CAGT)*, (TGAC)*, (CGAT)*, and (TAGC)*.

Cost is calculated as described above in terms of the number of steps necessary to synthesize the individual polymer strands 202 using each of the plurality reference sequences. Thus, in this example, each individual polymer strand S is associated with six cost values $c_1(S), \ldots, c_6(S)$ corresponding to a cost value for each of the representative reference sequences 302. The reference sequence that minimizes the cost of synthesizing S is identified for each of the individual polymer strands 202. This reference sequence is the lowest-cost reference sequence 400 for a given individual polymer strand 202.

A plurality of reference-sequence groups 402 are created in which all of the individual polymer strands 202 from the set of polymer strands to be synthesize 200 are grouped with their respective lowest-cost reference sequence 400. There may be a different number of individual polymer strands 202 in each reference-sequence group 402. One or more of the reference sequences may not be the lowest-cost reference sequence for any of the individual polymer strands 202. Thus, there may be no reference-sequence group 402 for one or more of the plurality of reference sequences. However, if the monomer sequences of the individual polymer strands 202 are statistically random and there is a large number of individual polymer strands 202, then each of the plurality of reference sequences will be associated with a reference-sequence group 402 and the number of individual polymer strands 202 in each reference-sequence group will be approximately equal.

Each reference sequence group 402, therefore, represents a subset of the set of polymer strands to be synthesized 200 that will all be synthesized using the same reference sequence (i.e., the lowest-cost reference sequence 400 for that group). This is the same relationship as described above in which a single reference sequence is used for the synthesis of all the polymer strands in a set of polymer strands. Accordingly, as described above, all of the individual polymer strands 202 within a reference sequence group 402 may be arranged in an ordering of polymer strands by the cost of synthesis 404. This ordering of polymer strands 404 may be divided into a plurality of cost-group batches 118 based on cost with batch partitions 406 that form batches of at most size M, the capacity of the synthesizer. This technique for forming batches is the same as shown in FIG. 2.

Figure 5:
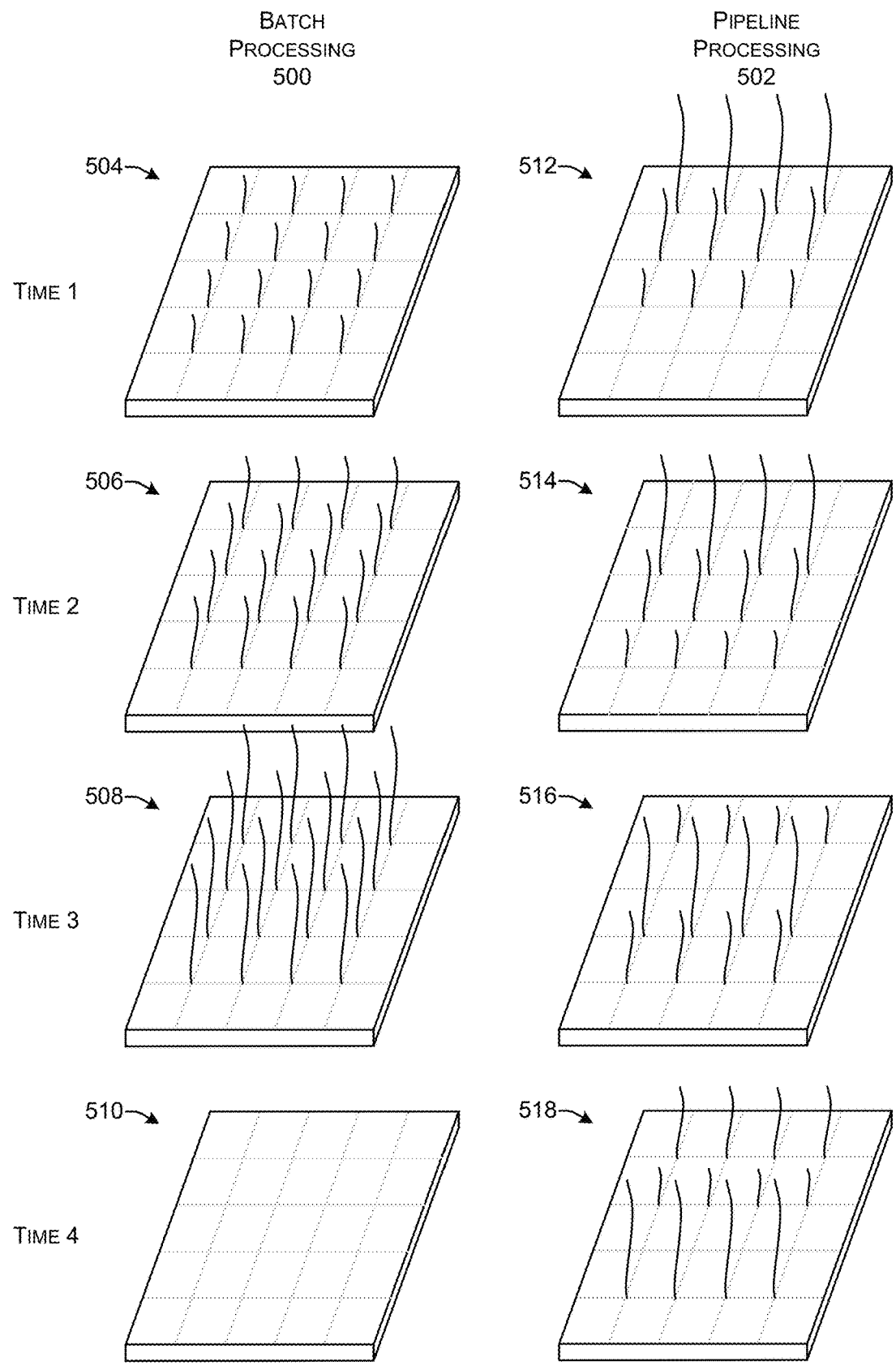
FIG. 5 illustrates the use of a flat substrate to synthesize polymers with batch processing and with pipeline processing.

FIG. 5 shows a schematic illustration of comparing the use of a flat substrate for synthesizing polymers with batch processing 500 and with pipeline processing 502. Four different time points are used to illustrate the dynamic growth of the polymer strands. The flat substrate may be an example of the solid support 124 introduced in FIG. 1. Polymers with different sequences may be grown at different locations on the flat substrate by using a technique which selectively de-protects individual polymer strands or clusters of polymer strands. Only the de-protected polymer strands are able to incorporate the nucleotide, or other type of monomer, provided by the synthesizer. Thus, selective de-protection controls which polymer strands may incorporate an additional monomer and the cycle of monomer addition specified by the reference sequence identifies the order which monomers are made available for incorporation.

Some techniques for selectively de-protecting growing polynucleotides are described in U.S. patent application Ser. No. 16/230,787 entitled "Selectively Controllable Cleavable Linkers" filed on Dec. 21, 2018 and in U.S. patent application entitled "Reversing Bias in Polymer Synthesis Electrode Array" filed concurrently with this application.

Batch processing 500 at time 1 as shown in view 504 has multiple short polymer strands attached to the surface of the solid support. If the sequences of the polymer strands are statistically random and each monomer subunit is presented equally for incorporation into the growing polymer strands, then all of the polymer strands will grow at approximately the same rate.

As polymer strands grow they become longer at time 2 shown in view 506. Time 3 illustrates in view 508 the polymer strands reaching their full length. This is the end of the batch synthesis. All the polymer strands are cleaved from the flat substrate at the same time using techniques described in the patent applications above or other techniques known in the art. View 510 shows the flat substrate at time 4 after cleavage of the polymer strands. The flat substrate may again be used to synthesize a new batch of polymer strands.

Pipeline processing 502 uses the flat substrate differently by growing polymer strands at different stages of synthesis simultaneously. Pipeline processing 502, like batch processing 500, uses selective de-protection to add specific monomers to individual ones of the growing polymer strands. Pipeline processing 502 also uses selective cleavage to cleave some but not all of the polymer strands from the surface of the flat substrate. Examples of suitable techniques for selectively cleaving less than all of the polymer strands growing on a flat substrate are described in U.S. patent application Ser. No. 16/230,787 entitled "Selectively Controllable Cleavable Linkers" filed on Dec. 21, 2018 and in U.S. patent application entitled "Reversing Bias in Polymer Synthesis Electrode Array" filed concurrently with this application.

View 512 shows three sets of polymer strands at different stages of synthesis. The longest polymer strands are illustrated at the rear, polymer strands in the middle have a medium length, and the shortest polymer strands that have started synthesis to most recently are shown towards the front of the flat substrate. All polymer strands growing on the same flat substrate are exposed to the same conditions and are synthesized using the same reference sequence. Stated differently, the sequence of monomer subunits physically flowed across the surface of the flat substrate is the same for all polymers bound to that substrate.

View 514 shows further progress of synthesis using pipeline processing 502. As synthesis has proceeded, the full-length polymer strands from the rear of the flat substrate in view 512 were cleaved, the polymer strands growing in the middle section of the flat substrate are becoming longer, and new polymer strands are starting to grow on the front of the flat substrate. Thus, in this example, there are polymer strands at three different stages of growth on the same flat substrate.

View 516 shows further growth and selective cleavage of the polymer strands on the flat substrate. Here, the newest polymer strands are growing on the rear of the substrate.

The process of growth, cleavage, and synthesis of new polymer strands continues during pipeline processing 502 as shown in view 518. After time 4, the pipeline process 502 may proceed to a state in which the length and arrangement of polymer strands are the same as view 512, but the sequences of the actual polymer strands attached to the flat substrate will be different than the polymer strands shown in view 512.

Although the arrangement of the growing polymer strands is shown in this example of pipeline processing 502 as arranged in rows, any separately addressable position on the surface of the flat substrate may be used independently from all other positions. Thus, the flat substrate may have a variety of different links of polymer strands attached to its surface with no particular structure or pattern as to the relative links of the growing polymer strands.

Pipeline processing 502 provides greater flexibility as compared to batch processing 500. One potential advantage of pipeline processing 502 is that the synthesizer is not idled as shown at time 4 in view 510. Pipeline processing 502 provides the ability to start growing new polymer strands without waiting for the synthesis of every polymer strand on the flat substrate to finish. Pipeline processing 502 also provides flexibility to use less than the full capacity of the flat substrate (which may be the capacity of the synthesizer) without tying up the remaining capacity.

Consider a request to synthesize fewer polymer strands than the capacity of the synthesizer can accommodate. With batch processing 500 synthesis is either delayed until there are requests to synthesize enough additional polymer strands to use the full capacity or synthesis proceeds without fully utilizing the capacity of the synthesizer. Thus, there is either a delay or the synthesizer is run at less than full capacity. However, with pipeline processing 502, synthesis can start immediately and any later-received requests for synthesis of polymer strands (provided the same reference sequence is suitable) may be added to the synthesizer while the synthesis of the first set of polymer strands continues.

Some polymer strands, even those placed in the same batch based on the cost of synthesis, will complete synthesis before other polymer strands. With pipeline processing 502 polymer strands that have reached their full length may be cleaved from the flat substrate and synthesis of a new polymer strand may be started at the same location. Thus, multiple polymer strands can be synthesized at the same position on the flat substrate.

Polymer strands that are synthesized at the same position on the flat substrate may be thought of as concatenated (although not physically connected) into long "super-strands." A super-strand may be "cut" to obtain the individual physical polymer strands. For example, if three DNA strands T-G-A, C-A-G, and C-T-G are all synthesized on the same position on the flat substrate, an oligonucleotide synthesizer will produce three DNA strands each with three nucleotides. A super-strand representing the activity of this position on the flat substrate will, however, be the concatenated sequence of T-G-A-C-A-G-C-T-G even though no such 9-mer nucleotide is synthesized.

The concept of super-strands and pipelining provides a way to manage the operation of synthesizers that is different from the batch synthesis concepts discussed elsewhere in this disclosure. Pipeline synthesis may begin by splitting all polymer strands into cost-grouped batches $\mathcal{B}_1, \ldots, \mathcal{B}_k$ as described before. One polymer strand from each batch is then concatenated into a super-strand. Thus, the super-strand will include one polymer strand from the lowest-cost batch, one from the highest-cost batch, and one from every batch with an intermediate cost. All the super-strands may then have similar synthesis costs because each includes a polymer strand from all of the cost-group batches.

The reference sequence for synthesizing strands from the batch $\mathcal{B}_i$ equals the original reference sequence used for synthesizing $\mathcal{B}_i$. Therefore, the cost of pipeline processing 502 is upper bounded by the cost of batch processing 500. Note however that even a simple greedy scheduling algorithm for pipeline processing 502 (i.e., not using intentionally constructed super-strands) with the reference sequence (ACGT)* gives a solution of cost≈μn if a large number of the polymer strands are synthesized at each location on the flat substrate. A simple greedy scheduling algorithm randomly selects the next polymer strand to synthesize once a position opens up on the flat substrate. Thus, pipeline processing 502, even without batching or creation of super-strands, achieves efficiencies that are close to the theoretical expectation for use of a single reference sequence.

Illustrative Processes

For ease of understanding, the processes discussed in this disclosure are delineated as separate operations represented as independent blocks. However, these separately delineated operations should not be construed as necessarily order dependent in their performance. The order in which the processes are described is not intended to be construed as a limitation, and unless other otherwise contradicted by context any number of the described process blocks may be combined in any order to implement the process or an alternate process. Moreover, it is also possible that one or more of the provided operations is modified or omitted.

FIGS. 6A-F show process 600 for processing data indicating sequences of a set of polymer strands in a way that enables efficient polymer synthesis. Process 600 may be implemented in various parts using one or more of the techniques shown in FIGS. 1-5.

At 602, data indicating the sequences of a set of polymer strands are received. This data may be the sequence data 103 introduced in FIG. 1. The sequences of the polymer strands may be designed, prior to the start of process 600, such that the monomer sequences are statistically random and/or that the monomer sequences do not include homopolymers.

At 604, a choice is made between synthesizing the set of polymer strands using a single reference sequence or using multiple reference sequences. If a single reference sequence is used, process 600 proceeds along the "no" path to steps shown on FIG. 6B. If multiple reference sequences are used for the synthesis then process 600 proceeds along the "yes" path. The reference sequence(s) may be designed so that each available monomer is used only once (e.g., (ACGT)*).

Figure 6A:
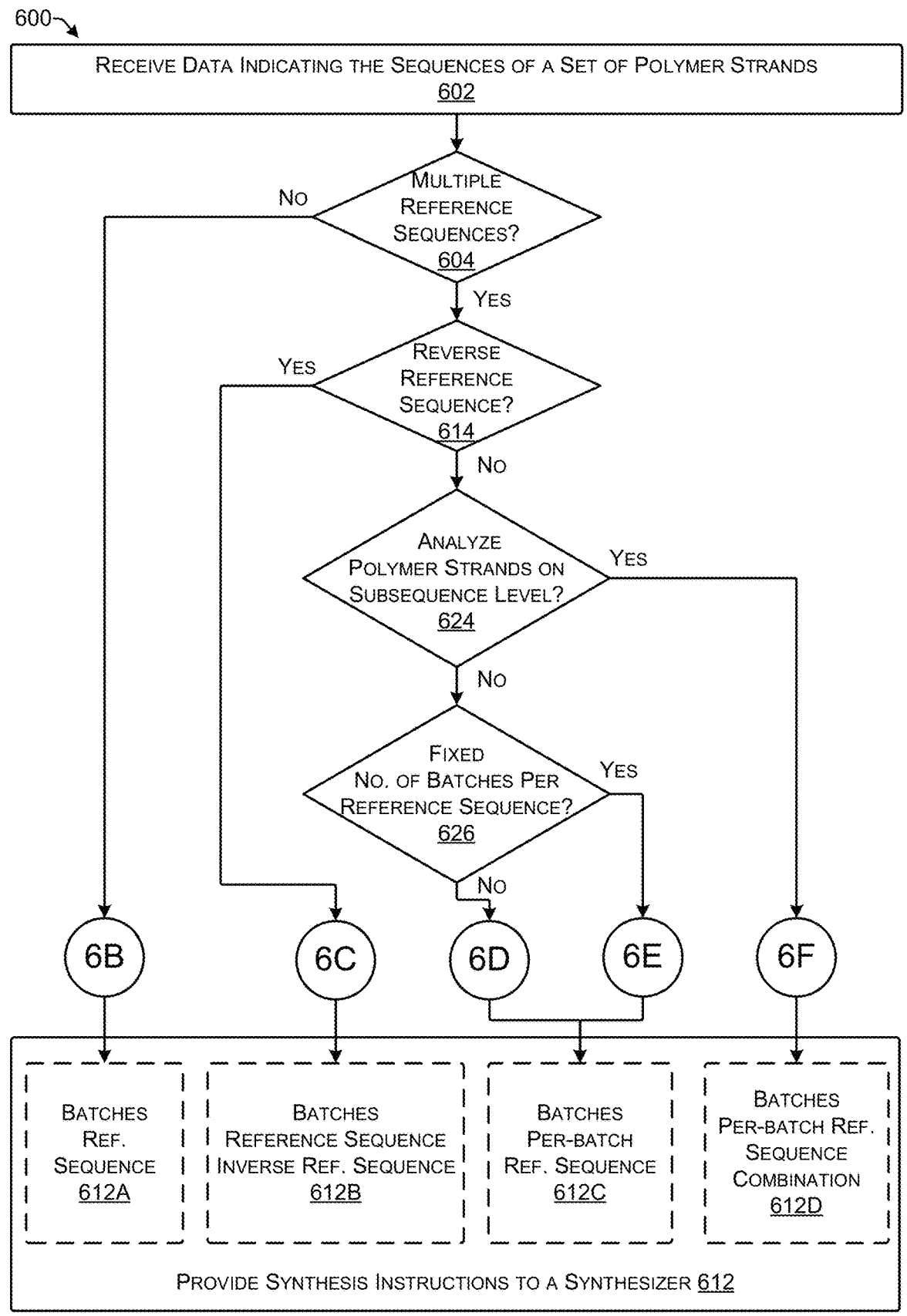
FIGS. 6A-6F are a flow diagram showing multiple illustrative processes for preparing data for synthesizer(s) in ways that enable the synthesizer(s) to efficiently synthesize polymers.
Figure 6B:
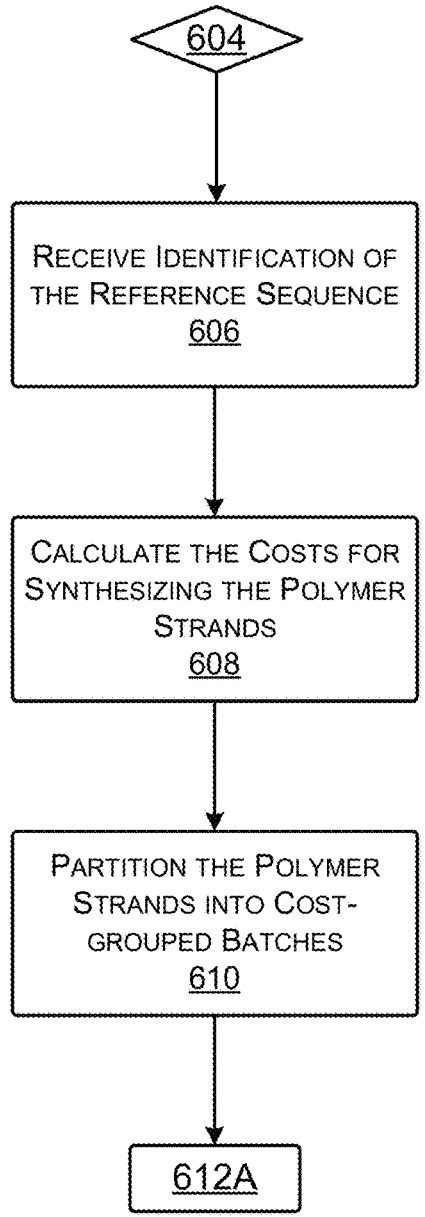
Figure 6C:
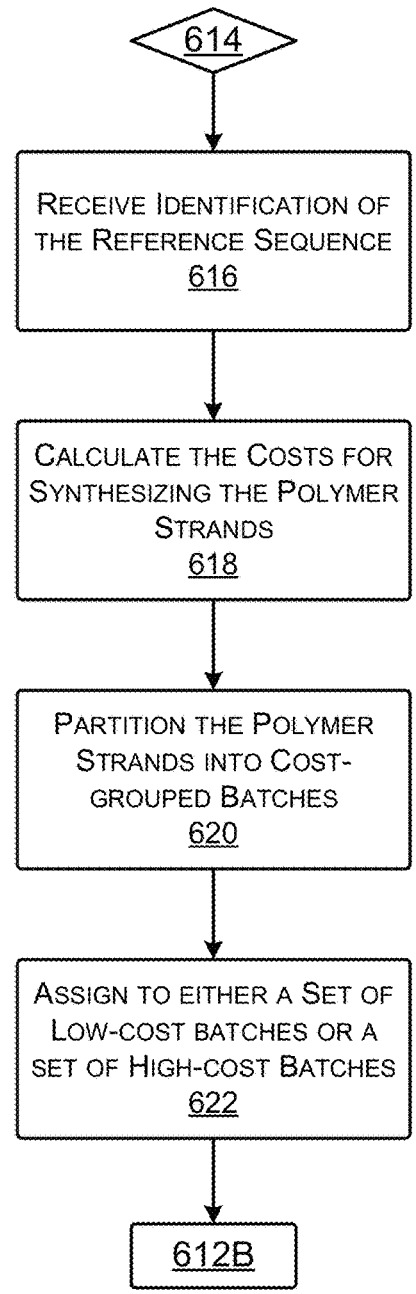
Figure 6D:
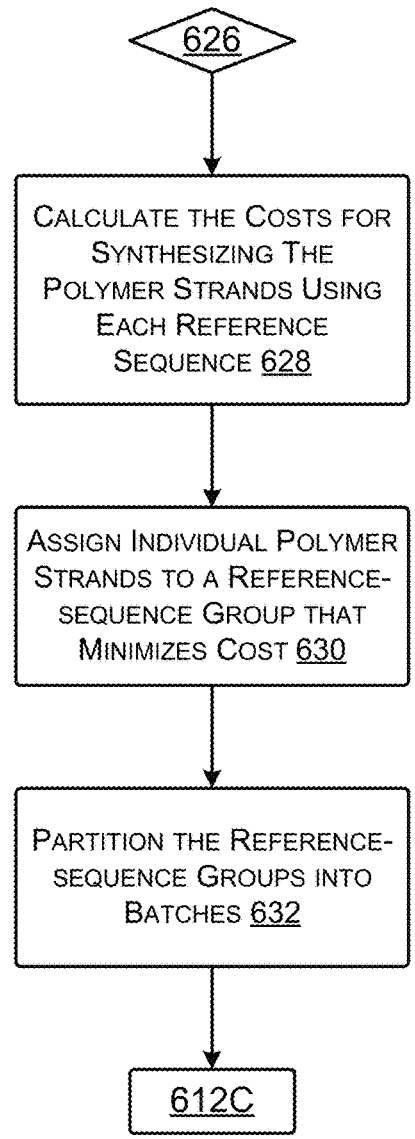

FIG. 6B shows that if use of a single reference sequence is selected, at 606, identification of the single reference sequence is received. Identification may be provided by a user inputting the reference sequence. Alternatively, the identification may be provided by computer system selecting a default reference sequence or selecting randomly from a predetermined set of reference sequences. As described above, one option for the reference sequence when synthesizing DNA is (ACGT)*

At 608, costs are calculated for synthesizing the individual polymer strands indicated in the data at 602 using the reference sequence identified at 606. The costs are calculated according to the techniques described above in which cost represents a number of steps of monomer addition required to synthesize the individual polymer strand.

At 610, the set of polymer strands is partitioned into cost-grouped batches. The cost-grouped batches may be the cost-grouped batches 118 shown in FIG. 1, FIG. 2, or FIG. 3. The size of the batches may represent the capacity of the synthesizer in terms of the number of polymer strands the synthesizer can synthesize simultaneously.

Returning to FIG. 6A, at 612A synthesis instructions are provided to the synthesizer. The synthesis instructions identify the cost-grouped batches of polymer strands (i.e., the sequences of individual strands that are included in each of the batches) and the reference sequence from 606. This information tells the synthesizer which strands to synthesize in the same batch and what order to provide the monomers for incorporation into the growing polymer strands.

If the polymer set is synthesized using multiple reference sequences then process 600 instead proceeds along the "yes" path from 604 to 614. At 614, it is determined if a reverse reference sequence will be used in addition to the reference sequence for a total of two reference sequences. For example, if the reference sequence is (ACGT)* then the reverse reference sequence will be (TGCA)*. If a reverse reference sequence is used, process 600 proceeds along the "yes" path to the steps shown on FIG. 6C.

At 616, identification of the reference sequence is received. Identification may be provided by a user inputting the reference sequence. Alternatively, the identification may be provided by computer system selecting a default reference sequence or selecting randomly from a predetermined set of reference sequences. The reverse reference sequence may also be identified or its sequence may be derived from the reference sequence.

At 618, costs are calculated for synthesizing the individual polymer strands indicated in the data at 602 using the reference sequence identified at 616. The costs are calculated according to the techniques described above in which cost represents a number of steps of monomer addition required to synthesize the individual polymer strand.

At 620, the set of polymer strands is partitioned into cost-grouped batches. The cost-grouped batches may be the cost-grouped batches 118 shown in FIG. 1, FIG. 2, or FIG. 3. The size of the batches may represent the capacity of the synthesizer in terms of the number of polymer strands the synthesizer can synthesize simultaneously.

At 622, individual ones of the cost-grouped batches of polymer strands are assigned to either a set of low-cost batches or a set of high-cost batches. This division of the cost-grouped batches into low-cost and high-cost is shown in the distribution of strands by cost 208 in FIG. 2. The reverse reference sequence is used to synthesize the high-cost half of the polymer strands.

Process 600 then proceeds from 622 to 612B on FIG. 6A. At 612B, the synthesizer is provided with instructions to synthesize the set of low-cost batches with the reference sequence and to synthesize the set of high-cost batches with the reverse reference sequence.

Returning now to 614, if multiple reference sequences are used (as determined at 604) but a reverse reference sequence is not used, process 600 proceeds along the "no" path from 614 to 624. At 624, it is determined if the polymer strands are analyzed at the subsequence level for use of two or more separate reference sequences to synthesize a single polymer strand. Different reference sequences may be used for different subsequences of a polymer strand by changing the sequence in which monomers are provided by the synthesizer part way through the synthesis. If multiple reference sequences are not used for a single polymer strand, then process 600 proceeds logged "no" path to 626.

At 626, it is determined if processing of the data for the synthesizer will be performed by assigning a fixed number of batches to each of the multiple reference sequences or not. If each reference sequence is not assigned a fixed number of batches, the process 600 proceeds along the "no" path to 628 on FIG. 6D.

At 628, the cost of synthesis for each of the individual polymer strands are calculated for each of a plurality of available reference sequences. This creates a plurality of cost values for each of the individual polymer strands. In an implementation, the plurality of available reference sequences may include two reference sequences such as a reference sequence and its corresponding reverse reference sequence (e.g., (ACGT)* and (TGCA)*). In an implementation, the plurality of available reference sequences may include the representative reference sequences 302 shown in FIG. 3 for a total of six different reference sequences.

At 630, each of the individual polymer strands is be assigned to a one of the plurality of reference sequences that minimizes cost thereby creating a plurality of reference-sequence groups. The reference-sequence groups may be the same as the reference-sequence groups 402 shown in FIG. 4. Each reference-sequence group is associated with one of the plurality of reference sequences and a number of individual polymer strands.

At 632, the reference-sequence groups are partitioned into batches based on the capacity of the synthesizer. The partitioning may be done simply by dividing the number of individual polymer strands into batches that do not exceed the capacity of the synthesizer. In an implementation, the batches may be cost-grouped batches and the partitioning may be performed based on the cost of synthesis for the individual polymer strands. Cost-based partitioning of polymer strands within a reference-sequence group is shown in FIG. 4. If cost-grouped batches of polymer strands are created at 632, the technique for creating the cost-grouped batches may be the same as the technique used at 610 in FIG. 6B.

Returning to FIG. 6A, at 612C, following the partitioning, synthesis instructions are provided to the synthesizer. The synthesis instructions identify the individual polymer strands in batches and the respective reference sequences used for each batch. This identifies a "per-batch reference sequence" that tells the synthesizer the order of monomers to add based on the sequences of the polymer strands in a given batch.

Figure 6E:
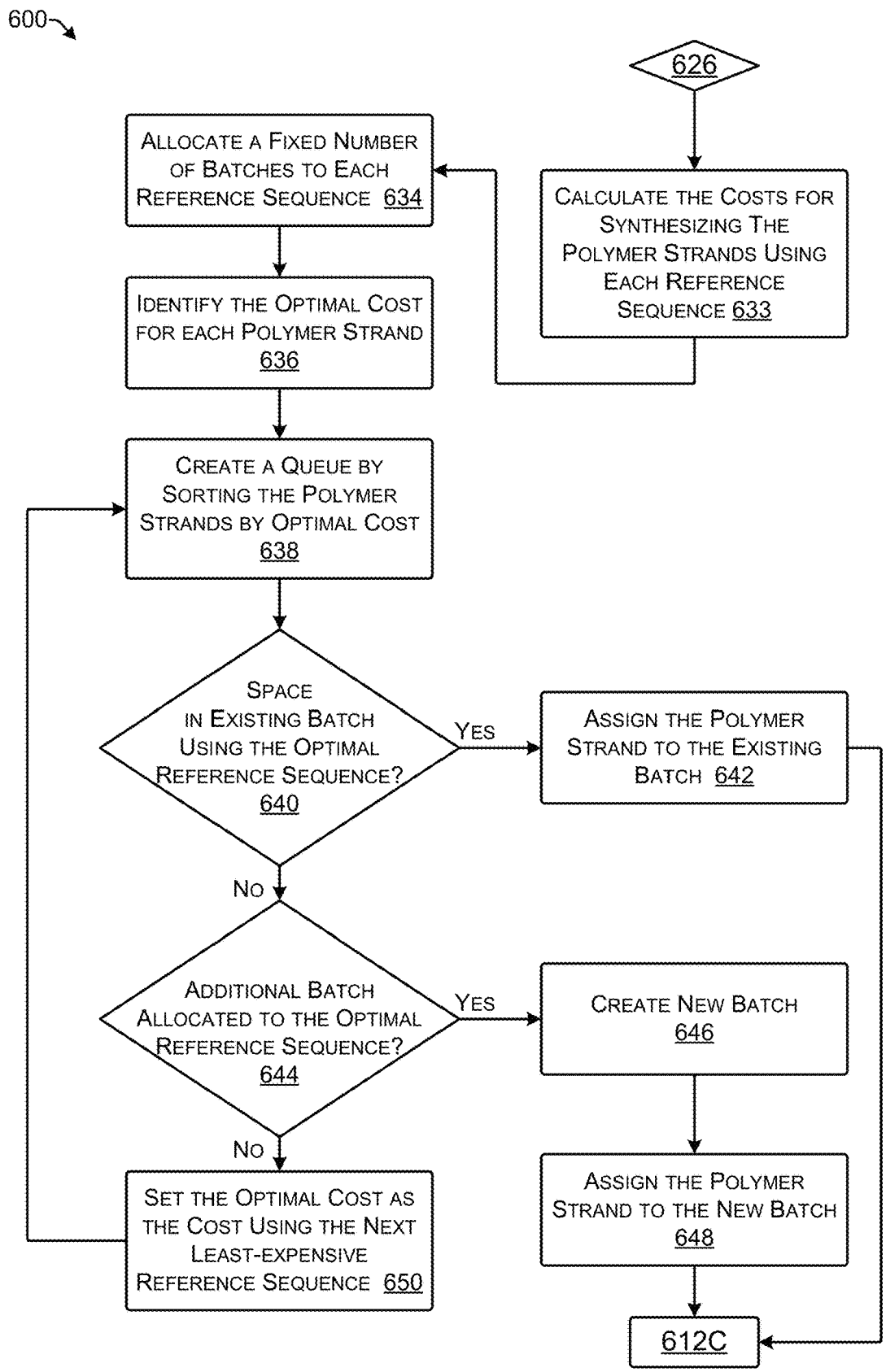

Returning now to 626, if a decision is made to assign a fixed number of batches to each of the multiple reference sequences then process 600 proceeds along the "yes" path to 633 on FIG. 6E.

At 633, the cost of synthesis for each of the individual polymer strands are calculated for each of a plurality of available reference sequences. This creates a plurality of cost values for each of the individual polymer strands. In an implementation, the plurality of available reference sequences may include two reference sequences such as a reference sequence and its corresponding reverse reference sequence (e.g., (ACGT)* and (TGCA)*). In an implementation, the plurality of available reference sequences may include the representative reference sequences 302 shown in FIG. 3 for a total of six different reference sequences.

At 634, a fixed number of batches is allocated to each reference sequence. The allocation of batch capacity to individual reference sequences may be equal or unequal (i.e., some reference sequences may be allocated more or fewer batches than other reference sequences).

At 636, the "optimal cost" is identified for each polymer strand in the set of polymer strands include in the data received at 602. The optimal cost of is the cost of synthesis using the reference sequence that yields the lowest cost out of all the available reference sequences. This reference sequence is referred to as the "optimal reference sequence". Thus, the optimal cost represents the lowest possible cost of synthesis for a given polymer strand.

At 638, a queue or ranked listing of the polymer strands by optimal cost is created. This may simply be a data structure that includes the monomer sequence of each polymer strand, a cost value, and the reference sequence that yields the cost value. The entries in this data structure may then be sorted by cost value. When a polymer strand is assigned to a batch for synthesis, the polymer strand is removed from the queue. Thus, once the queue is empty, the instructions for efficient polymer synthesis are complete.

At 640, it is determined if, for the polymer strand from the queue with the lowest optimal cost, there is space available in an existing batch that uses the reference sequence which produces the optimal cost for that polymer strand. Thus, process 600 checks to see if there is already a partially full batch using the optimal reference sequence for the polymer strand at the "front" of the queue. If so, process 600 proceeds along the "yes" path to 642.

At 642, the polymer strand from the queue with the lowest optimal cost is assigned to the existing batch that uses the optional reference sequence for that polymer strand. The polymer strand is then removed from the queue, the polymer strand with the next lowest optimal cost moves to the front of the queue, and the available space for polymer strands in the batch is reduced by one.

If, however, any existing batches that use the optimal reference sequence are full, process 600 proceeds along "no" path to 644. At 644, it is determined if there are any additional batches allocated to the optimal reference sequence. Recall that at 634, a fixed number of batches is allocated to each reference sequence. Thus, if there are many polymer strands that have the same reference sequence as their respective optimal reference sequence, then it is possible that the full allocation of batches to that reference sequence may be used.

If it is possible to create a new batch for the optimal reference sequence, process 600 proceeds from 644 along the "yes" path to 646. At 646, a new batch using the optimal reference sequence is created.

At 648, the polymer strand is assigned to this new batch. This new batch becomes an existing batch containing only one polymer strand. Thus, during a subsequent iteration another polymer strand from the queue that uses the same optimal reference sequence may be placed in this batch.

If they are no longer any unallocated batches for the optimal reference sequence, then process 600 proceeds from 644 along "no" path to 650. Thus, at this point, all of the batches which use optimal reference sequence for this polymer strand or full and it is not possible to create any additional batches using the same reference sequence.

At 650, the optimal cost for this reference sequence is set as the cost for using the next lease type expensive reference sequence. For example, because the "best" reference sequence is not available for use with this polymer strand, the "second best" reference sequence is considered optimal and the second lowest cost of synthesis becomes the optimal cost. If a polymer strand is unable to be placed in a batch over multiple rounds the optimal cost, and optimal reference sequence, will iteratively be shifted from the best to the second best then to the third best, and so on.

After the optimal cost has been redefined as the cost of synthesis using the next most efficient reference sequence, process 600 returns to 638 where the cost value for the polymer strand is updated in the queue. This may change the position of the polymer strand in the queue by moving it farther down the queue because the cost value has increased. This process is repeated until all polymer strands, ending with the polymer strand having the highest cost, are assigned to a batch.

Returning to FIG. 6A, now that all polymer strands are assigned to a batch and each batch is associated with a reference sequence, at 612C instructions are provided to the synthesizer. The synthesis instructions identify the batches and the per-batch reference sequence. Note that due to the polymer strand allocation process shown on FIG. 6E there may be some polymer strands assigned to batches that do not use the cost-minimizing reference sequence for those polymer strands. Even so, this process provides for efficient synthesis of the entire set of polymer strands as shown in FIGS. 7-9.

Figure 6F:
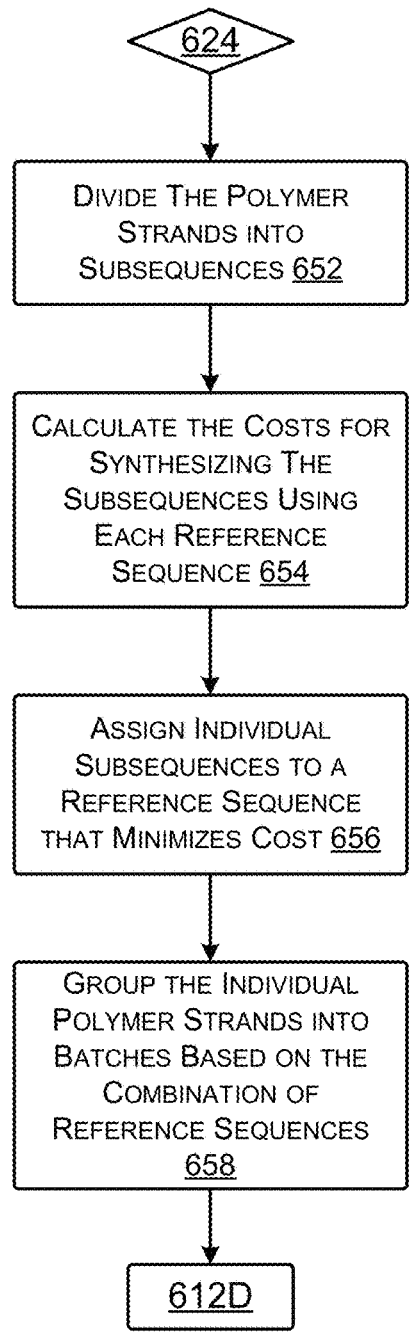

Returning now to 624, if a decision is made to analyze the polymer strands at the subsequence level and assign reference sequences based on subsequences within individual polymer strands, then process 600 proceeds along "yes" path to 652 on FIG. 6F.

At 652, the individual polymer strands are divided into two or more subsequences. For example, a DNA strand that is 200 nucleotides long could be divided into two subsequences each of 100 nucleotides. Analysis of each subsequence, each 100-nucleotide portion, could proceed using one of the techniques described previously to identify a lowest-cost reference sequence for that subsequence. If the two, or more, subsequences are most efficiently synthesized with different reference sequences, then synthesis may be performed by switching the reference sequence midway through the growth of the DNA strand.

Using a reference sequence that is best suited for a particular subsequence of a polymer strand can increase efficiency by more precisely focusing the use of the reference sequences, but additional costs are incurred for each transition during synthesis from one reference sequence to the next. Therefore, dividing a polymer strand into too many subsequences may decrease efficiency.

For a very large number of batches, k, it is possible to improve efficiency further than previous techniques by considering reference sequences that are concatenations of blocks $(ACGT)^{s'}$ and $(TGCA)^{s'}$ for some s'. Concatenating reference sequences is the same as using different reference sequences for different sub-portions of a polymer strand. Each polymer strand is then assigned to the best concatenated reference sequence for that polymer strand. To analyze this algorithm, split every polymer strand into blocks (or subsequences) of size s. Let $4s' \approx 2s - \sqrt{4s/3\pi}$. As described above, each block of lengths can be manufactured using a reference sequence $(ACGT)^{s'}$ or $(TGCA)^{s'}$. The cost of synthesizing the entire polymer strand is thus approximately equal to $$\underbrace{\frac{n}{s}}_{\text{\# blocks}} \times \underbrace{\left(2s - \sqrt{\frac{4s}{3\pi}}\right)}_{\text{cost per block}} + \underbrace{\left(\frac{n}{s} - 1\right)}_{\text{block boundary effects}} =$$

$$2n - \sqrt{\frac{4}{3\pi}} \frac{n}{\sqrt{s}} + \left(\frac{n}{s} - 1\right).$$

The number of blocks represents the number of subsequences that the polymer strands are divided into. The cost per block represents the cost of synthesizing each subsequence using the reference sequence for that subsequence. Block boundary effects are the cost of switching from one reference sequences to another.

At 654, the cost of synthesis for the subsequences using each reference sequence is calculated. This identifies which reference sequence is the lowest cost for a given subsequence of a one of the polymer strands.

At 656, individual subsequences are assigned to the reference sequence that minimizes cost.

At 658, the individual polymer strands are grouped into batches based on the combination of reference sequences used for the respective subsequences. All the polymer strands in a given batch are synthesized using the same reference sequence or combination of reference sequences. For example, if individual DNA strands are divided into two subsequences then all DNA strands that have the lowest cost of synthesis with the combination of reference sequences (ACGT)* and (CGAT)* will be grouped into the same one or more batches. However, DNA strands that are most efficiently synthesized with a different combination of reference sequences, even (CGAT)* followed by (ACGT)*, must be placed in a different batch.

At 612D on FIG. 6A, synthesis instructions are provided to the synthesizer. The synthesis instructions identify the batches of individual polymer strands and the per-batch reference sequence combination to use when synthesizing each of the batches. Thus, instead of identifying a single reference sequence per-batch as in 612C, instructions provided at 612D indicate two or more reference sequences and the point during synthesis at which to transition from one reference sequence to the next.

Examples

Table 4 shows the results of cost calculations for the simulated synthesis of a set of DNA strands comprising the canonical nucleotides A, G, C, and T. All DNA strands in this example have length 105 and randomly generated sequences. The randomly generated sequences of the individual DNA strands are constrained for some tests to exclude homopolymers. The reference sequence (ACGT)* was used for all simulations. All synthesis was simulated using a single batch that contains a number of strands indicated in the "strand count" column. The experimental results are similar to the calculated upper bound values shown in Table 1.

TABLE 4

Simulated synthesis costs for single batch sequencing using a single reference sequence.

| | cost ($S$) ± standard deviation | |
|---|---|---|
| Strand count $|S|$ | w/o homopolymers | w/ homopolymers |
| 500,000 | 250 ± 2.15 | 315.5 ± 2.5 |
| 1,000,000 | 251.1 ± 2 | 317.1 ± 2.8 |
| 2,000,000 | 251.75 ± 1.75 | 319.1 ± 3.2 |
| 4,000,000 | 253 ± 2.17 | 321.1 ± 3 |

FIGS. 7-9 show line graphs comparing the cost of synthesizing DNA strands to the number of batches synthesized. All DNA strands in these examples comprise the canonical nucleotides A, G, C, and T. Each graph shown in FIGS. 7-9 compares the results of four different ways of processing the DNA strand sequence data for synthesis.

The naïve method uses random or first-come-first-served assignment of DNA strands to batches. The reference sequence for the naïve method is (ACGT)*, but any of the reference sequences shown in FIG. 3 will produce identical results. The naïve method does not use any of the techniques presented in this disclosure and results in the highest cost. The cost of synthesis using the naïve method does not change with the number of batches. The naïve method is indicated by a thin black line.

Method 1 uses the same reference sequence as the naïve method, (ACGT)*; however, all DNA strands are sorted by the cost of synthesis and placed in cost-grouped batches. Any of the reference sequences shown in FIG. 3 will produce identical results with this method. The lowest-cost batches are processed first. Method 1 uses the technique shown in FIG. 2 for creating cost-grouped batches. The benefits of Method 1 increase as the number of batches increases eventually approaching a cost of 2× strand length for strands without homopolymers and 2.5× strand length for strands with homopolymers as predicted. Method 1 is indicated with a dashed line.

Method 2 uses the reference sequence (ACGT)* from some of the batches and the reverse reference sequence (TGCA)* for the other batches. However, any of the reference sequences shown in FIG. 3 and the corresponding reverse reference sequence will produce identical results. The cost of synthesizing each of the DNA strands is calculated for the reference sequence and for the reverse reference sequence. Each of the DNA strands is then assigned to the one of the two reference sequences that minimizes cost. This creates two reference-sequence groups and the DNA strands within each reference-sequence group are sorted by cost and grouped into batches. Method 2 uses the technique shown in FIG. 4 modified to use only two reference-sequence groups. Method 2 is able to reduce the synthesis cost below that of Method 1 once there are about five or more batches. Typical usage scenarios for applications such as digital data storage will frequently involve many more than five batches. Method 2 is indicated with a dotted line.

Method 3 uses six different reference sequences: (ACGT)*, (TGCA)*, (CAGT)*, (TGAC)*, (CGAT)*, and (TAGC)*. These are the representative reference sequences 302 shown in FIG. 3. However, any other combination of six reference sequences from any column of the table 300 in FIG. 3 will produce identical results. The cost of synthesizing each of the DNA strands is calculated for each of the six reference sequences. Each of the six reference sequences is assigned a certain number of batches. A given reference sequence may be assigned to zero batches if it is not a good match for the sequences to be synthesized. Thus, there is no requirement to use every available reference sequence.

In one example, if a total of 60 batches needed to synthesize all the DNA strands S in a set of DNA strands $\mathcal{S}$, then each of the six reference sequences may be assigned 10 batches. In another example, a first reference sequence may be assigned 20 batches, four more reference sequences may each be assigned 10 batches, and one reference sequence may be assigned zero batches (i.e., the reference sequence is not used). After a batch is assigned to one of the reference sequences, the number of available batches remaining for allocation is decreased by one. Batch assignment may proceed in a manner that matches a reference sequence with a set of DNA strands in a way that minimizes the synthesis cost.

For example, for each DNA strand S, the cost of synthesis is calculated using each of the available reference sequences. The reference sequences for this method are all of the representative reference sequences 302 shown in FIG. 3: (ACGT)*, (TGCA)*, (CAGT)*, (TGAC)*, (CGAT)*, and (TAGC)*. Thus, each individual DNA strand S is associated with six cost values $c_1(S), \ldots, c_6(S)$. The optimal cost of S is defined as the lowest cost from $c_1(S), \ldots, c_6(S)$. Thus, opt. $\text{cost}(S) = \min(c_1(S), \ldots, c_6(S))$. That is, the optimal cost of S is the cost of synthesis using the reference sequence that yields the lowest cost out of all the available reference sequences (the "optimal reference sequence").

All DNA strands S in a set of DNA strands $\mathcal{S}$ are sorted by optimal cost in increasing order (i.e., DNA strands with lower optimal costs are placed ahead of DNA strands with higher optimal costs). This creates a queue of DNA strands ordered by optimal cost.

One-by-one DNA strands from the queue are placed into a batch $\mathcal{B}$ if possible starting with the lowest cost strand. Each DNA strand is allocated to a batch according to the following process. If there is space in an existing batch that uses the optimal reference sequence, then the DNA strand is assigned into that batch. If there is no space in any batches using the optimal reference sequence, but there is at least one additional batch allocated to that reference sequence (recall that all reference sequences are initially allocated a set number of batches), then a new batch is created for that reference sequence and the DNA strand is placed in that new batch. If, however, there is no space in any batches using the optimal reference sequence and all batches for that reference sequence have already been allocated, then the cost of synthesis using the next least expensive reference sequence (i.e., the second lowest cost from $c_1(S), \ldots, c_6(S)$) is taken as the optimal cost and the DNA strand with this new, higher optimal cost is returned to the queue.

This process repeats until all DNA strands from the queue have been allocated to a batch. Thus, every DNA strand may not be allocated to a batch that uses the optimal reference sequence, but the total cost of synthesizing all the batches $\mathcal{B}$ to create the set of DNA strands $\mathcal{S}$ is minimized.

Method 3 uses the technique shown in FIG. 6E. Method 3 produces the lowest synthesis cost of any of the methods compared in FIGS. 7-9. Method 3 is indicated with a thick black line.

Figure 7A:
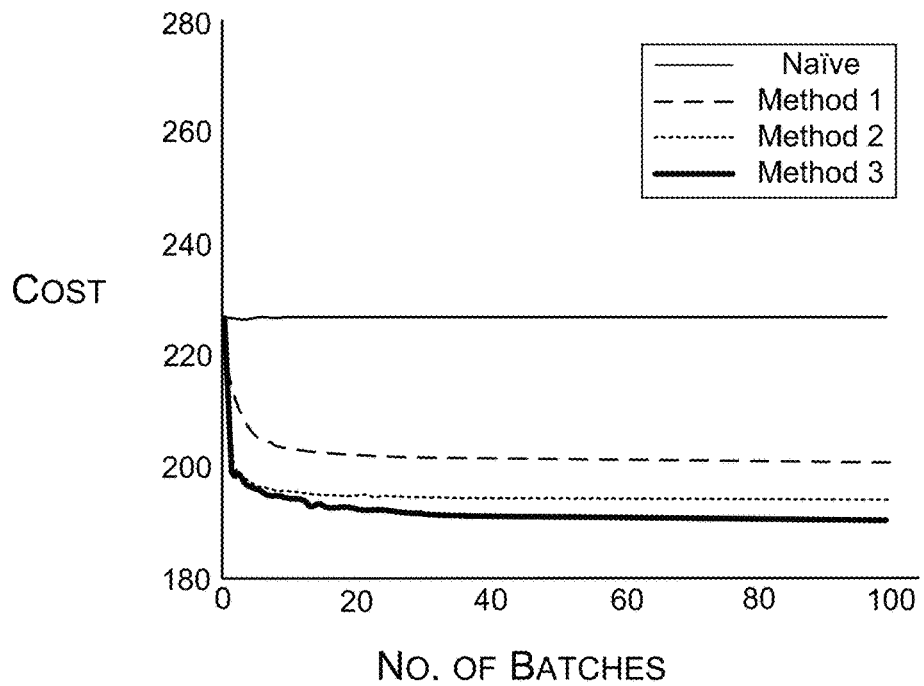
FIG. 7A is a line graph showing the cost of synthesis versus the number of batches for DNA strands of length 100 without homopolymers that are grouped into batches of 1000 DNA strands.

FIG. 7A shows how an increase in the number of batches affects synthesis cost for DNA strands of length 100 without homopolymers that are grouped into batches containing 1000 DNA strands.

Figure 7B:
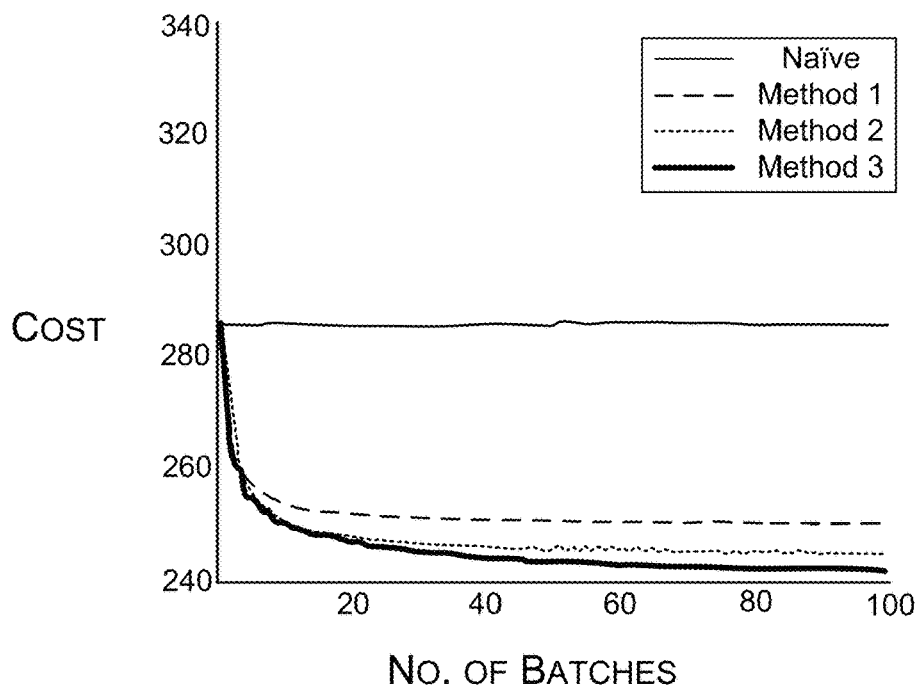
FIG. 7B is a line graph showing the cost of synthesis versus the number of batches for DNA strands of length 100 with homopolymers that are grouped into batches of 1000 DNA strands.

FIG. 7B shows how an increase in the number of batches affects synthesis cost for DNA strands of length 100 with homopolymers that are grouped into batches containing 1000 DNA strands.

Figure 8A:
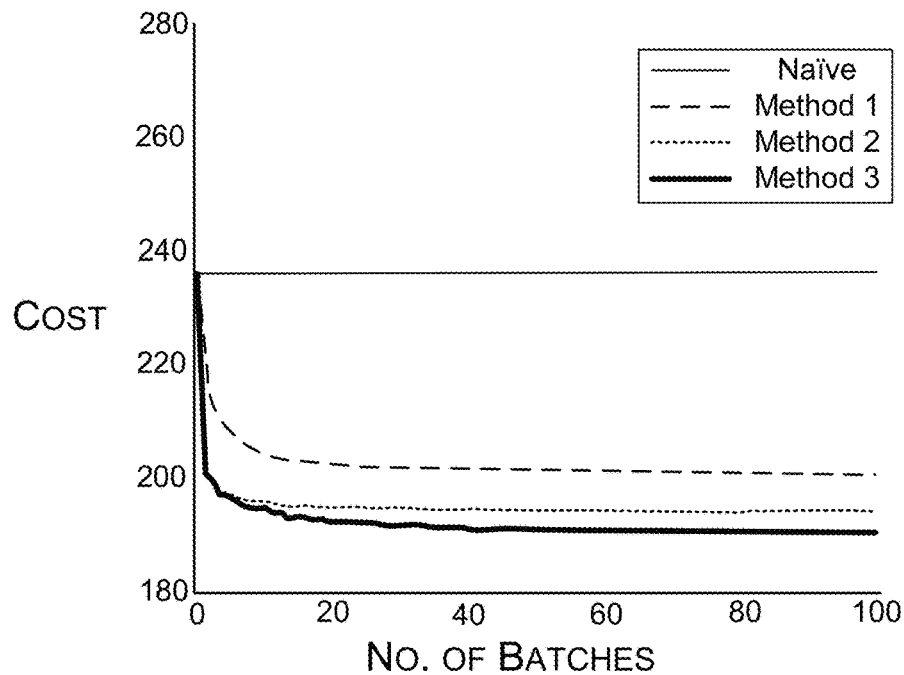
FIG. 8A is a line graph showing the cost of synthesis versus the number of batches for DNA strands of length 100 without homopolymers that are grouped into batches of 100,000 DNA strands.

FIG. 8A shows how an increase in the number of batches affects synthesis cost for DNA strands of length 100 without homopolymers that are grouped into batches containing 100,000 DNA strands.

Figure 8B:
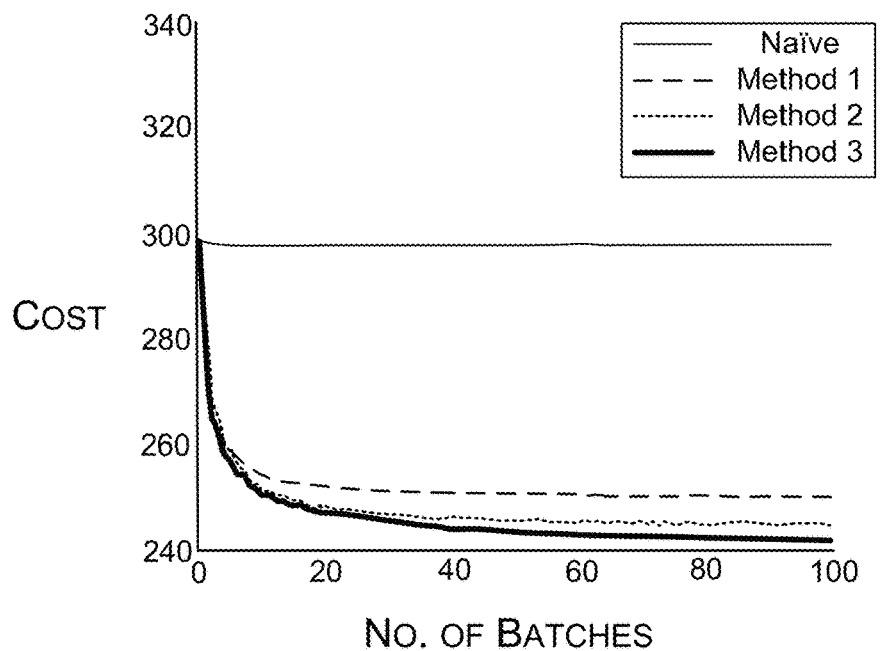
FIG. 8B is a line graph showing the cost of synthesis versus the number of batches for DNA strands of length 100 with homopolymers that are grouped into batches of 100,000 DNA strands.

FIG. 8B shows how an increase in the number of batches affects synthesis cost for DNA strands of length 100 with homopolymers that are grouped into batches containing 100,000 DNA strands.

Figure 9A:
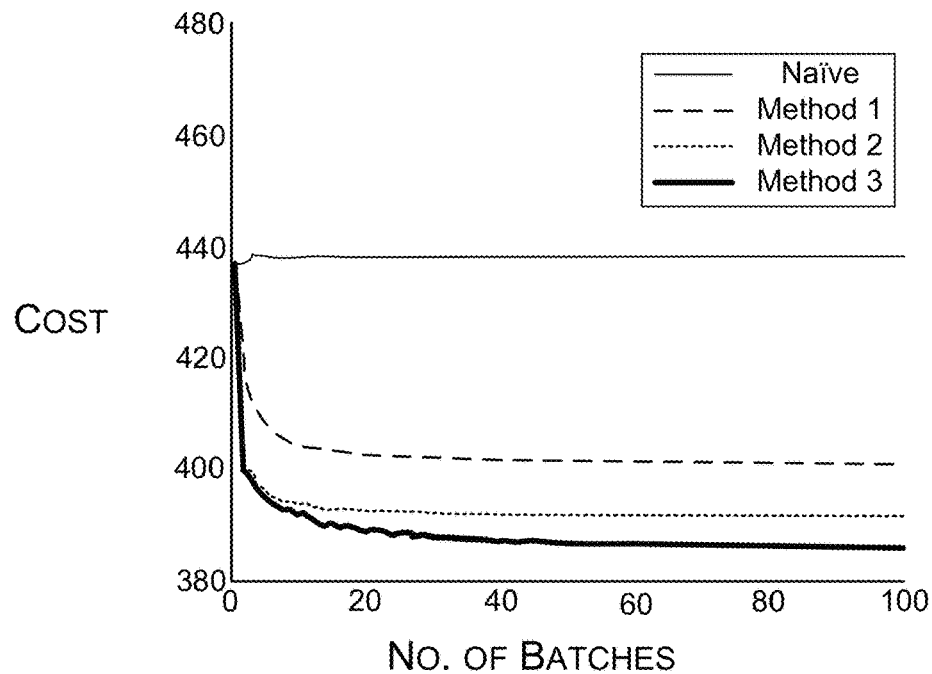
FIG. 9A is a line graph showing the cost of synthesis versus the number of batches for DNA strands of length 200 without homopolymers that are grouped into batches of 1000 DNA strands.

FIG. 9A shows how an increase in the number of batches affects synthesis cost for DNA strands of length 200 without homopolymers that are grouped into batches containing 1000 DNA strands.

Figure 9B:
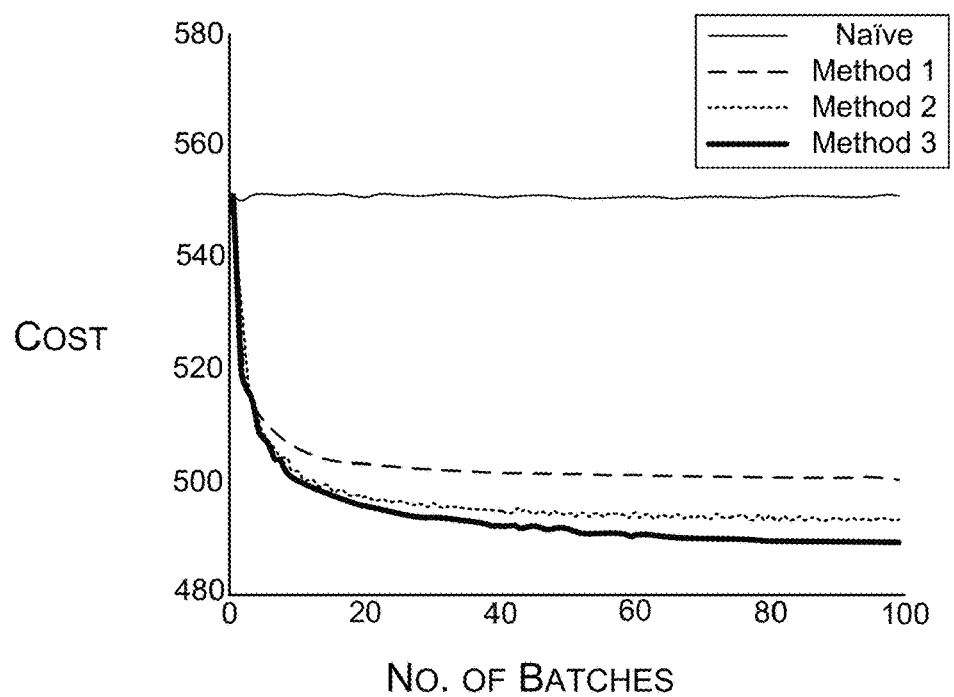
FIG. 9B is a line graph showing the cost of synthesis versus the number of batches for DNA strands of length 200 with homopolymers that are grouped into batches of 1000 DNA strands.

FIG. 9B shows how an increase in the number of batches affects synthesis cost for DNA strands of length 200 with homopolymers that are grouped into batches containing 1000 DNA strands.

Illustrative Computer Architecture

Figure 10:
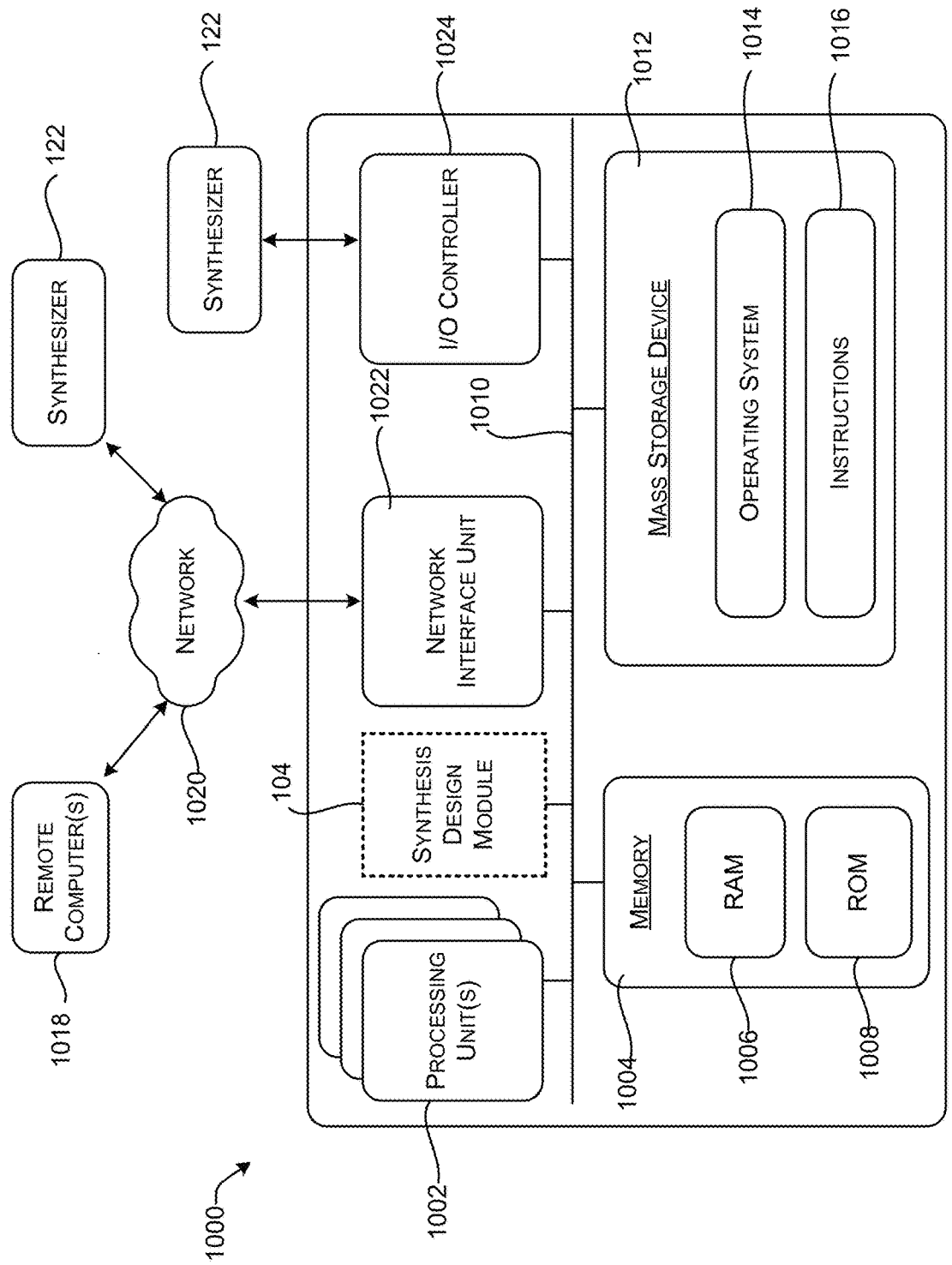
FIG. 10 is an illustrative computer architecture for implementing techniques of this disclosure.

FIG. 10 is a computer architecture diagram showing an illustrative computer hardware and software architecture for a computing device such as the computing device 102 introduced FIG. 1. In particular, the computer 1000 illustrated in FIG. 10 can be utilized to implement the synthesis design module 104.

The computer 1000 includes one or more processing units 1002, a system memory 1004, including a random-access memory 1006 ("RAM") and a read-only memory ("ROM") 1008, and a system bus 1010 that couples the memory 1004 to the processing unit(s) 1002. A basic input/output system ("BIOS" or "firmware") containing the basic routines that help to transfer information between elements within the computer 1000, such as during startup, can be stored in the ROM 1008. The computer 1000 further includes a mass storage device 1012 for storing an operating system 1014 and other instructions 1016 that represent application programs and/or other types of programs such as, for example, instructions to implement the synthesis design module 104. The mass storage device 1012 can also be configured to store files, documents, and data.

The mass storage device 1012 is connected to the processing unit(s) 1002 through a mass storage controller (not shown) connected to the bus 1010. The mass storage device 1012 and its associated computer-readable media provide non-volatile storage for the computer 1000. Although the description of computer-readable media contained herein refers to a mass storage device, such as a hard disk, CD-ROM drive, DVD-ROM drive, or USB storage key, it should be appreciated by those skilled in the art that computer-readable media can be any available computer-readable storage media or communication media that can be accessed by the computer 1000.

Communication media includes computer readable instructions, data structures, program modules, or other data in a modulated data signal such as a carrier wave or other transport mechanism and includes any delivery media. The term "modulated data signal" means a signal that has one or more of its characteristics changed or set in a manner so as to encode information in the signal. By way of example, and not limitation, communication media includes wired media such as a wired network or direct-wired connection, and wireless media such as acoustic, radio frequency, infrared and other wireless media. Combinations of any of the above should also be included within the scope of computer-readable media.

By way of example, and not limitation, computer-readable storage media can include volatile and non-volatile, removable and non-removable media implemented in any method or technology for storage of information such as computer-readable instructions, data structures, program modules or other data. For example, computer-readable storage media includes, but is not limited to, RAM 1006, ROM 1008, EPROM, EEPROM, flash memory or other solid-state memory technology, CD-ROM, digital versatile disks ("DVD"), HD-DVD, BLU-RAY, 4K Ultra BLU-RAY, or other optical storage, magnetic cassettes, magnetic tape, magnetic disk storage or other magnetic storage devices, or any other medium that can be used to store the desired information and which can be accessed by the computer 1000. For purposes of the claims, the phrase "computer-readable storage medium," and variations thereof, does not include waves or signals per se or communication media.

According to various configurations, the computer 1000 can operate in a networked environment using logical connections to a remote computer(s) 1018 through a network such as the network 1020. The computer 1000 can connect to the network 1020 through a network interface unit 1022 connected to the bus 1010. It should be appreciated that the network interface unit 1022 can also be utilized to connect to other types of networks and remote computer systems. The computer 1000 can also include an input/output controller 1024 for receiving and processing input from a number of other devices, including a keyboard, mouse, touch input, an electronic stylus (not shown), or equipment such as a synthesizer 122 for synthesizing polymers such as polynucleotides. Similarly, the input/output controller 1024 can provide output to a display screen or other type of output device (not shown).

It should be appreciated that the software components described herein, when loaded into the processing unit(s) 1002 and executed, can transform the processing unit(s) 1002 and the overall computer 1000 from a general-purpose computing device into a special-purpose computing device customized to facilitate the functionality presented herein. The processing unit(s) 1002 can be constructed from any number of transistors or other discrete circuit elements, which can individually or collectively assume any number of states. More specifically, the processing unit(s) 1002 can operate as a finite-state machine, in response to executable instructions contained within the software modules disclosed herein. These computer-executable instructions can transform the processing unit(s) 1002 by specifying how the processing unit(s) 1002 transitions between states, thereby transforming the transistors or other discrete hardware elements constituting the processing unit(s) 1002.

Encoding the software modules presented herein can also transform the physical structure of the computer-readable media presented herein. The specific transformation of physical structure depends on various factors, in different implementations of this description. Examples of such factors include, but are not limited to, the technology used to implement the computer-readable media, whether the computer-readable media is characterized as primary or secondary storage, and the like. For example, if the computer-readable media is implemented as semiconductor-based memory, the software disclosed herein can be encoded on the computer-readable media by transforming the physical state of the semiconductor memory. For instance, the software can transform the state of transistors, capacitors, or other discrete circuit elements constituting the semiconductor memory. The software can also transform the physical state of such components to store data thereupon.

As another example, the computer-readable media disclosed herein can be implemented using magnetic or optical technology. In such implementations, the software presented herein can transform the physical state of magnetic or optical media, when the software is encoded therein. These transformations can include altering the magnetic characteristics of particular locations within given magnetic media. These transformations can also include altering the physical features or characteristics of particular locations within given optical media, to change the optical characteristics of those locations. Other transformations of physical media are possible without departing from the scope and spirit of the present description, with the foregoing examples provided only to facilitate this discussion.

In light of the above, it should be appreciated that many types of physical transformations take place in the computer 1000 to store and execute the software components presented herein. It also should be appreciated that the architecture shown in FIG. 10 for the computer 1000, or a similar architecture, can be utilized to implement many types of computing devices such as desktop computers, notebook computers, servers, supercomputers, gaming devices, tablet computers, and other types of computing devices known to those skilled in the art. For example, the computer 1000 may be wholly or partially integrated into the synthesizer 122. It is also contemplated that the computer 1000 might not include all of the components shown in FIG. 10, can include other components that are not explicitly shown in FIG. 10, or can utilize an architecture completely different than that shown in FIG. 10.

Illustrative Embodiments

The following clauses described multiple possible embodiments for implementing the features described in this disclosure. The various embodiments described herein are not limiting nor is every feature from any given embodiment required to be present in another embodiment. Any two or more of the embodiments may be combined together unless context clearly indicates otherwise. As used herein in this document "or" means and/or. For example, "A or B" means A without B, B without A, or A and B. As used herein, "comprising" means including all listed features and potentially including addition of other features that are not listed. "Consisting essentially of" means including the listed features and those additional features that do not materially affect the basic and novel characteristics of the listed features. "Consisting of" means only the listed features to the exclusion of any feature not listed.

Clause 1. A method for efficient synthesis of polymer strands, the method comprising: receiving sequence data (103) indicating monomer sequences (116) of individual polymer strands (202) in a set of polymer strands (200); receiving identification of a reference sequence (120, 302, 304, 402); calculating a cost of synthesis for the individual polymer strands (202) using the reference sequence (120, 302, 304, 402); partitioning the set of polymer strands (200) into cost-grouped batches of polymer strands (118) based on the cost of synthesis for the individual polymer strands (202); and providing synthesis instructions (114) identifying the cost-grouped batches of polymer strands (118) and the reference sequence (120, 302, 304, 402) to a synthesizer (122).

Clause 2. The method of clause 1, wherein the polymer strands comprise polynucleotides, the monomers comprise nucleosides, and the synthesizer comprises an oligonucleotide synthesizer.

Clause 3. The method of any of clauses 1-2, wherein the sequences of the monomers of the individual polymer strands are statistically random.

Clause 4. The method of any of clauses 1-3, wherein the individual polymer strands do not include homopolymers.

Clause 5. The method of any of clauses 1-4, wherein a shortest repeating sequence of the reference sequence includes each monomer only once.

Clause 6. The method of any of clauses 1-5, wherein providing the synthesis instructions identifying the cost-grouped batches of polymer strands and the reference sequence to the synthesizer includes causing the synthesizer to synthesize the cost-grouped batches of polymer strands by adding monomers in an order indicated by the reference sequence.

Clause 7. The method of any of clauses 1-6, further comprising assigning individual ones of the cost-grouped batches of polymer strands into either a set of low-cost batches or a set of high-cost batches based on the cost of synthesizing the individual ones of the cost-grouped batches using the reference sequence; and wherein providing the synthesis instructions identifying the cost-grouped batches of polymer strands and the reference sequence to the synthesizer includes providing instructions to synthesize the set of low-cost batches using the reference sequence and instructions to synthesize the set of high-cost batches using a reverse reference sequence.

Clause 8. A system for efficient synthesis of polymer strands, the system comprising: one or more processing units (1002); memory (1012) coupled to the one or more processing units; and instructions (1016) stored in the memory (1012) that when executed by the one or more processing units (1002) cause the system to: receive sequence data (103) indicating monomer sequences (116) of individual polymer strands (202) in a set of polymer strands (200); calculate a cost of synthesis for ones of the individual polymer strands (202) using a plurality of reference sequences (302, 402); assign ones of the individual polymer strands (202) to a one of the plurality of reference sequences (302, 402) that minimizes cost thereby creating a plurality of reference-sequence groups (400) each associated with a respective reference sequence (302, 402); partition one of the reference-sequence groups (400) into batches (118) based on a capacity of a synthesizer (122); and provide synthesis instructions (114) identifying the individual polymer strands (202) in the batches (118) and the respective reference sequences (302, 402) to the synthesizer.

Clause 9. The system of clause 8, wherein the individual polymer strands comprise polynucleotides and the monomers comprise nucleosides.

Clause 10. The system of any of clauses 8-9, wherein the instructions further cause the system to: for the one of the reference-sequence groups, partition the set of polymer strands into cost-grouped batches of polymer strands based on the cost of synthesis for the individual polymer strands in the one of the reference-sequence groups using the reference sequence assigned to the one of the reference-sequence groups; and wherein the batches are the cost-grouped batches.

Clause 11. The system of any of clauses 8-10, wherein the plurality of reference sequences consists of a first reference sequence and a second reference sequence with a sequence that is a reverse of the first reference sequence.

Clause 12. The system of any of clauses 8-11, wherein a number of different monomers is four and the plurality of reference sequences consists of six reference sequences of length four, wherein each of the six reference sequences includes all four of the different monomers and wherein there is no shared sequence of length three within any of the six reference sequences.

Clause 13. The system of any of clauses 8-12, wherein the instructions further cause the system to: divide individual ones of the individual polymer strands into two subsequences; calculate a cost of synthesis for the two subsequences using each of the plurality of reference sequences; assign individual ones of the subsequences of the polymer strands to a one of the plurality of reference sequences that minimizes cost; and wherein the reference-sequence groups comprise the subsequences of the polymer strands.

Clause 14. The system of any of clauses 8-13, further comprising the synthesizer, wherein the synthesizer is an oligonucleotide synthesizer and wherein the instructions further cause the system to cause the synthesizer to synthesize the set of polymer strands.

Clause 15. Computer-readable storage media (1012) storing instructions (1016) that, when executed by one or more processing units (1002), cause a system to perform acts comprising: receiving sequence data (103) indicating monomer sequences (116) of individual polymer strands (202) in a set of polymer strands (200); partitioning the set of polymers strands into cost-grouped batches (118) based on costs of synthesizing the individual polymer strands (202) using one or more reference sequences (120, 302, 304, 402); and providing synthesis instructions (114) identifying the cost-grouped batches (118) of the individual polymer strands (202) and the one or more reference sequences (120, 302, 304, 402) to a synthesizer (122).

Clause 16. The computer-readable storage media of clause 15, wherein: the one or more reference sequences consists of a single reference sequence with a sequence that uses each type of monomer only once; the partitioning comprises ordering the individual polymer strands based on a cost of synthesis with the single reference sequence to create an ordered ranking of the individual polymer strands; and the instructions further cause the system to perform acts comprising partitioning the ordered ranking into the cost-grouped batches based on a capacity of the synthesizer.

Clause 17. The computer-readable storage media of any of clauses 15-16, wherein: the one or more reference sequences consists of a first reference sequence and a second reference sequence with a sequence that is a reverse of the first reference sequence; and providing the synthesis instructions identifying the cost-grouped batches of polymer strands and the one or more reference sequences to the synthesizer comprises providing instructions to synthesize a batch of the cost-grouped batches with the one of the first reference sequence or the second reference sequence that minimizes a cost of synthesis for the batch.

Clause 18. The computer-readable storage media of any of clauses 15-17, wherein: the one or more reference sequences comprises a plurality of reference sequences; the instructions further cause the system to perform acts comprising: assigning individual ones of the individual polymer strands to one of the plurality of reference sequences that minimizes a cost of synthesis for the individual ones of the individual polymer strands thereby creating a plurality of reference-sequence groups each associated with a respective reference sequence; and providing the synthesis instructions identifying the cost-grouped batches of polymer strands and the one or more reference sequences to the synthesizer comprises providing instructions to synthesize the cost-grouped batches in each of the plurality of reference-sequence groups with the respective reference sequence.

Clause 19. The computer-readable storage media of any of clauses 15-18, wherein the instructions further cause the system to perform acts comprising: calculating a cost of synthesis for each of the individual polymer strands using each of the one or more reference sequences; identifying, for each of the individual polymer strands, an optimal reference sequence that yields the lowest cost out of all of the one or more reference sequences; sorting the individual polymer strands based on cost of synthesis using the respective optimal reference sequence for each of the individual polymer strands; and wherein the partitioning the set of polymer strands into cost-grouped batches comprises assigning at least a portion of the individual polymer strands to a cost-grouped batch that will be synthesized using the optimal reference sequence for the portion of the individual polymer strands.

Clause 20. The computer-readable storage media of any of clauses 15-19, wherein: the one or more reference sequences comprises a plurality of reference sequences; the instructions further cause the system to perform acts comprising: dividing an individual polymer strand into two subsequences; calculating costs of synthesis for each of the two subsequences using each of the plurality of reference sequences; and assigning each of the subsequences to a one of the plurality of reference sequences that minimizes cost; and the partitioning the set of polymer strands into cost-grouped batches is based on a first reference sequence and a second reference sequence assigned to the two subsequences of the individual polymer strand.

CONCLUSION

Although the subject matter has been described in language specific to structural features and/or methodological acts, it is to be understood that the subject matter defined in the appended claims is not necessarily limited to the specific features or acts described above. Rather, the specific features and acts are disclosed as example forms of implementing the claims.

The terms "a," "an," "the" and similar referents used in the context of describing the invention are to be construed to cover both the singular and the plural unless otherwise indicated herein or clearly contradicted by context. The terms "based on," "based upon," and similar referents are to be construed as meaning "based at least in part" which includes being "based in part" and "based in whole," unless otherwise indicated or clearly contradicted by context. The terms "portion," "part," or similar referents are to be construed as meaning at least a portion or part of the whole including up to the entire noun referenced. As used herein, "approximately" or "about" or similar referents denote a range of ±10% of the stated value.

Certain embodiments are described herein, including the best mode known to the inventors for carrying out the invention. Of course, variations on these described embodiments will become apparent to those of ordinary skill in the art upon reading the foregoing description. Skilled artisans will know how to employ such variations as appropriate, and the embodiments disclosed herein may be practiced otherwise than specifically described. Accordingly, all modifications and equivalents of the subject matter recited in the claims appended hereto are included within the scope of this disclosure. Moreover, any combination of the above-described elements in all possible variations thereof is encompassed by the invention unless otherwise indicated herein or otherwise clearly contradicted by context.

Furthermore, references have been made to publications, patents and/or patent applications throughout this specification. Each of the cited references is individually incorporated herein by reference for its particular cited teachings as well as for all that it discloses.

The invention claimed is:

1. A method for efficient synthesis of polymer strands, the method comprising:
receiving sequence data indicating monomer sequences of individual polymer strands in a set of polymer strands;
receiving identification of a reference sequence;
calculating a cost of synthesis for the individual polymer strands using the reference sequence;

partitioning the set of polymer strands into cost-grouped batches of polymer strands based on the cost of synthesis for the individual polymer strands; and providing synthesis instructions identifying the cost-grouped batches of polymer strands and the reference sequence to a synthesizer, wherein providing the synthesis instructions identifying the cost-grouped batches of polymer strands and the reference sequence to the synthesizer includes causing the synthesizer to synthesize the cost-grouped batches of polymer strands by adding monomers in an order indicated by the reference sequence.

2. The method of claim 1, wherein the polymer strands comprise polynucleotides, the monomers comprise nucleosides, and the synthesizer comprises an oligonucleotide synthesizer.

3. The method of claim 1, wherein the sequences of the monomers of the individual polymer strands are statistically random.

4. The method of claim 1, wherein the individual polymer strands do not include homopolymers.

5. The method of claim 1, wherein a shortest repeating sequence of the reference sequence includes each monomer only once.

6. The method of claim 1, further comprising assigning individual ones of the cost-grouped batches of polymer strands into either a set of low-cost batches or a set of high-cost batches based on the cost of synthesizing the individual ones of the cost-grouped batches using the reference sequence; and wherein providing the synthesis instructions identifying the cost-grouped batches of polymer strands and the reference sequence to the synthesizer includes providing instructions to synthesize the set of low-cost batches using the reference sequence and instructions to synthesize the set of high-cost batches using a reverse reference sequence.

7. The method of claim 1, wherein the polymer strands comprise deoxyribose nucleic acid (DNA) and the synthesizer is an oligonucleotide synthesizer.

8. A system for efficient synthesis of polymer strands, the system comprising:
one or more processing units;
memory coupled to the one or more processing units;
instructions stored in the memory that when executed by the one or more processing units cause the system to:
receive sequence data indicating monomer sequences of individual polymer strands in a set of polymer strands;
calculate a cost of synthesis for ones of the individual polymer strands using a plurality of reference sequences;
assign ones of the individual polymer strands to a one of the plurality of reference sequences that minimizes cost thereby creating a plurality of reference-sequence groups each associated with a respective reference sequence;
partition one of the reference-sequence groups into batches based on a capacity of a synthesizer; and
provide synthesis instructions identifying the individual polymer strands in the batches and the respective reference sequences to the synthesizer; and
the synthesizer, wherein the synthesis instructions cause the synthesizer to synthesize the set of polymer strands according to the identified batches.

9. The system of claim 8, wherein the individual polymer strands comprise polynucleotides and the monomers comprise nucleosides.

10. The system of claim 8, wherein the instructions further cause the system to:
for the one of the reference-sequence groups, partition the set of polymer strands into cost- grouped batches of polymer strands based on the cost of synthesis for the individual polymer strands in the one of the reference-sequence groups using the reference sequence assigned to the one of the reference-sequence groups; and
wherein the batches are the cost-grouped batches.

11. The system of claim 8, wherein the plurality of reference sequences consists of a first reference sequence and a second reference sequence with a sequence that is a reverse of the first reference sequence.

12. The system of claim 8, wherein a number of different monomers is four and the plurality of reference sequences consists of six reference sequences of length four, wherein each of the six reference sequences includes all four of the different monomers and wherein there is no shared sequence of length three within any of the six reference sequences.

13. The system of claim 8, wherein the instructions further cause the system to:
divide individual ones of the individual polymer strands into two subsequences;
calculate a cost of synthesis for the two subsequences using each of the plurality of reference sequences;
assign individual ones of the subsequences of the polymer strands to a one of the plurality of reference sequences that minimizes cost; and
wherein the reference-sequence groups comprise the subsequences of the polymer strands.

14. The system of claim 8, wherein the polymer strands comprise deoxyribose nucleic acid (DNA) and the synthesizer is an oligonucleotide synthesizer.

15. Computer-readable storage media storing instructions that, when executed by one or more processing units, cause a system to perform acts comprising:
receiving sequence data indicating monomer sequences of individual polymer strands in a set of polymer strands;
partitioning the set of polymers strands into cost-grouped batches based on costs of synthesizing the individual polymer strands using one or more reference sequences, wherein a reference sequence is an order in which a synthesizer provides monomers for addition to polymer strands during synthesis; and
providing synthesis instructions that cause the synthesizer to synthesize the set of polymer strands in the cost-grouped batches and by providing the monomers in one or more orders specified by the one or more reference sequences.

16. The computer-readable storage media of claim 15, wherein:
the one or more reference sequences consists of a single reference sequence with a sequence that uses each type of monomer only once;
the partitioning comprises ordering the individual polymer strands based on a cost of synthesis with the single reference sequence to create an ordered ranking of the individual polymer strands; and
the instructions further cause the system to perform acts comprising partitioning the ordered ranking into the cost-grouped batches based on a capacity of the synthesizer.

17. The computer-readable storage media of claim 15, wherein:
- the one or more reference sequences consists of a first reference sequence and a second reference sequence with a sequence that is a reverse of the first reference sequence; and
- providing the synthesis instructions identifying the cost-grouped batches of polymer strands and the one or more reference sequences to the synthesizer comprises providing instructions to synthesize a batch of the cost-grouped batches with the one of the first reference sequence or the second reference sequence that minimizes a cost of synthesis for the batch.

18. The computer-readable storage media of claim 15, wherein:
- the one or more reference sequences comprises a plurality of reference sequences;
- the instructions further cause the system to perform acts comprising: assigning individual ones of the individual polymer strands to one of the plurality of reference sequences that minimizes a cost of synthesis for the individual ones of the individual polymer strands thereby creating a plurality of reference-sequence groups each associated with a respective reference sequence; and
- providing the synthesis instructions identifying the cost-grouped batches of polymer strands and the one or more reference sequences to the synthesizer comprises providing instructions to synthesize the cost-grouped batches in each of the plurality of reference-sequence groups with the respective reference sequence.

19. The computer-readable storage media of claim 15, wherein the instructions further cause the system to perform acts comprising:
- calculating a cost of synthesis for each of the individual polymer strands using each of the one or more reference sequences;
- identifying, for each of the individual polymer strands, an optimal reference sequence that yields the lowest cost out of all of the one or more reference sequences;
- sorting the individual polymer strands based on cost of synthesis using the respective optimal reference sequence for each of the individual polymer strands; and
- wherein the partitioning the set of polymer strands into cost-grouped batches comprises assigning at least a portion of the individual polymer strands to a cost-grouped batch that will be synthesized using the optimal reference sequence for the portion of the individual polymer strands.

20. The computer-readable storage media of claim 15, wherein:
- the one or more reference sequences comprises a plurality of reference sequences;
- the instructions further cause the system to perform acts comprising:
  - dividing an individual polymer strand into two subsequences;
  - calculating costs of synthesis for each of the two subsequences using each of the plurality of reference sequences; and
  - assigning each of the subsequences to a one of the plurality of reference sequences that minimizes cost; and
- the partitioning the set of polymer strands into cost-grouped batches is based on a first reference sequence and a second reference sequence assigned to the two subsequences of the individual polymer strand.

* * * * *